(12) United States Patent
Bergeron et al.

(10) Patent No.: US 7,734,102 B2
(45) Date of Patent: Jun. 8, 2010

(54) METHOD AND SYSTEM FOR SCREENING CARGO CONTAINERS

(75) Inventors: Eric Bergeron, Quebec (CA); Luc Perron, Charlesbourg, Quebec (CA); Alain Bergeron, Sainte-Foy (CA)

(73) Assignee: Optosecurity Inc., Quebec (CA)

( * ) Notice: Subject to any disclaimer, the term of this patent is extended or adjusted under 35 U.S.C. 154(b) by 1093 days.

(21) Appl. No.: 11/268,749

(22) Filed: Nov. 8, 2005

(65) Prior Publication Data

US 2006/0257005 A1    Nov. 16, 2006

Related U.S. Application Data

(63) Continuation-in-part of application No. PCT/CA2005/000716, filed on May 11, 2005.

(51) Int. Cl.
| | |
|---|---|
| G06K 9/00 | (2006.01) |
| G06K 9/62 | (2006.01) |
| G06K 9/64 | (2006.01) |
| G06K 9/68 | (2006.01) |
| G01N 23/04 | (2006.01) |
| G01B 3/44 | (2006.01) |
| G01B 3/52 | (2006.01) |
| G01B 5/28 | (2006.01) |

(52) U.S. Cl. .................. 382/209; 382/100; 382/132; 382/141; 382/151; 382/152; 382/215; 382/216; 382/217; 382/218; 382/220; 378/57; 702/34; 702/35

(58) Field of Classification Search ............. 382/100, 382/132, 141, 151, 152, 209, 215–220; 378/57; 702/34, 35
See application file for complete search history.

(56) References Cited

U.S. PATENT DOCUMENTS

| 4,338,626 A | 7/1982 | Lemelson |
| 4,379,348 A | 4/1983 | Haas et al. |

(Continued)

FOREIGN PATENT DOCUMENTS

| CA | 2307439 | 5/2000 |

(Continued)

OTHER PUBLICATIONS eXaminer 3DX, Explosives Detection Systems, L3 Communications, Security & Detection Systems, Nov. 8-9, 2005.

(Continued)

*Primary Examiner*—Anand Bhatnagar
*Assistant Examiner*—Randolph Chu

(57) ABSTRACT

A system for screening cargo containers is provided including an image generation device, an apparatus for screening cargo containers and an output module. The image generation device generates an image signal conveying information related to the contents of the cargo container. The apparatus receives the image signal and a list of objects conveying objects expected to be present in the cargo container. A processing unit processes the image signal in combination with the list of objects and a group of target images associated with objects to derive mismatch information data. The mismatch information data conveys at least one distinction between the list of objects and the information related to the contents of the cargo container conveyed by the image signal. Information conveying the mismatch information data is released and conveyed to a user of the system by an output module.

57 Claims, 11 Drawing Sheets

U.S. PATENT DOCUMENTS

| | | |
|---|---|---|
| 4,383,327 A | 5/1983 | Kruger |
| 4,418,575 A | 12/1983 | Hundt et al. |
| 4,470,303 A | 9/1984 | O'Donnell |
| 4,480,899 A | 11/1984 | Sprague |
| 4,482,958 A | 11/1984 | Nakayama et al. |
| 4,509,075 A | 4/1985 | Simms et al. |
| 4,573,198 A | 2/1986 | Anderson |
| 4,612,666 A | 9/1986 | King |
| 4,637,056 A | 1/1987 | Sherman et al. |
| 4,651,297 A | 3/1987 | Schlunt |
| 4,653,109 A | 3/1987 | Lemelson et al. |
| 4,722,096 A | 1/1988 | Dietrich et al. |
| 4,724,543 A | 2/1988 | Klevecz et al. |
| 4,725,733 A | 2/1988 | Horman et al. |
| 4,736,399 A | 4/1988 | Okazaki |
| 4,736,401 A | 4/1988 | Donges et al. |
| 4,737,650 A | 4/1988 | West |
| 4,756,015 A | 7/1988 | Doenges et al. |
| 4,759,047 A | 7/1988 | Donges et al. |
| 4,775,895 A | 10/1988 | Traupe et al. |
| 4,783,794 A | 11/1988 | Dietrich |
| 4,788,704 A | 11/1988 | Donges et al. |
| 4,795,253 A | 1/1989 | Sandridge et al. |
| 4,819,188 A | 4/1989 | Matsubara et al. |
| 4,832,447 A | 5/1989 | Javidi |
| 4,837,733 A | 6/1989 | Shiraishi et al. |
| 4,838,644 A | 6/1989 | Ochoa et al. |
| 4,841,554 A | 6/1989 | Doenges et al. |
| 4,849,912 A | 7/1989 | Leberl et al. |
| 4,862,358 A | 8/1989 | Kimura et al. |
| 4,869,574 A | 9/1989 | Hartman |
| 4,870,670 A | 9/1989 | Geus |
| 4,884,289 A | 11/1989 | Glockmann et al. |
| 4,887,899 A | 12/1989 | Hung |
| 4,916,722 A | 4/1990 | Ema |
| 4,955,060 A | 9/1990 | Katsuki et al. |
| 5,003,616 A | 3/1991 | Orita et al. |
| 5,018,178 A | 5/1991 | Katsumata |
| 5,020,111 A | 5/1991 | Weber |
| 5,022,062 A | 6/1991 | Annis |
| 5,034,812 A | 7/1991 | Rawlings |
| 5,041,993 A | 8/1991 | Rawlings |
| 5,056,130 A | 10/1991 | Engel |
| 5,060,249 A | 10/1991 | Eisen et al. |
| 5,063,602 A | 11/1991 | Peppers et al. |
| 5,065,418 A | 11/1991 | Bermbach et al. |
| 5,073,782 A | 12/1991 | Huguenin et al. |
| 5,079,698 A | 1/1992 | Grenier et al. |
| 5,091,924 A | 2/1992 | Bermbach et al. |
| 5,107,351 A | 4/1992 | Leib et al. |
| 5,109,276 A | 4/1992 | Nudelman et al. |
| 5,132,811 A | 7/1992 | Iwaki et al. |
| 5,132,842 A | 7/1992 | Yeh |
| 5,132,998 A | 7/1992 | Tsutsui et al. |
| 5,138,167 A | 8/1992 | Barnes |
| 5,150,229 A | 9/1992 | Takesue et al. |
| 5,179,581 A | 1/1993 | Annis |
| 5,181,234 A | 1/1993 | Smith |
| 5,198,669 A | 3/1993 | Namiki et al. |
| 5,216,541 A | 6/1993 | Takesue et al. |
| 5,239,595 A | 8/1993 | Takemura et al. |
| 5,257,085 A | 10/1993 | Ulich et al. |
| 5,257,322 A | 10/1993 | Matsuoka et al. |
| 5,268,967 A | 12/1993 | Jang et al. |
| 5,283,641 A | 2/1994 | Lemelson |
| 5,297,222 A | 3/1994 | Mori et al. |
| 5,309,244 A | 5/1994 | Katagiri et al. |
| 5,309,523 A | 5/1994 | Iwaki et al. |
| 5,311,359 A | 5/1994 | Lucas et al. |
| 5,319,547 A | 6/1994 | Krug et al. |
| 5,323,472 A | 6/1994 | Falk |
| 5,327,286 A | 7/1994 | Sampsell et al. |
| 5,345,081 A | 9/1994 | Rogers |
| 5,345,173 A | 9/1994 | Bito et al. |
| 5,365,560 A | 11/1994 | Tam |
| 5,365,564 A | 11/1994 | Yashida et al. |
| 5,367,552 A | 11/1994 | Peschmann |
| 5,371,542 A | 12/1994 | Pauli et al. |
| 5,375,156 A | 12/1994 | Kuo-Petravic et al. |
| 5,376,796 A | 12/1994 | Chan et al. |
| 5,379,334 A | 1/1995 | Zimmer et al. |
| 5,379,336 A | 1/1995 | Kramer et al. |
| 5,418,380 A | 5/1995 | Simon et al. |
| 5,420,788 A | 5/1995 | Vissers |
| 5,425,113 A | 6/1995 | Ito |
| 5,428,657 A | 6/1995 | Papanicolopoulos et al. |
| 5,430,787 A | 7/1995 | Norton |
| 5,481,584 A | 1/1996 | Tang et al. |
| 5,481,622 A | 1/1996 | Gerhardt et al. |
| 5,483,569 A | 1/1996 | Annis |
| 5,485,312 A | 1/1996 | Horner et al. |
| 5,490,218 A | 2/1996 | Krug et al. |
| 5,493,444 A | 2/1996 | Khoury et al. |
| 5,506,880 A | 4/1996 | Scardino et al. |
| 5,519,225 A | 5/1996 | Mohr et al. |
| 5,524,133 A | 6/1996 | Neale et al. |
| 5,528,702 A | 6/1996 | Mitsuoka et al. |
| 5,528,703 A | 6/1996 | Lee |
| 5,546,189 A | 8/1996 | Svetkoff et al. |
| 5,568,256 A | 10/1996 | Korner et al. |
| 5,580,471 A | 12/1996 | Fukumoto et al. |
| 5,595,767 A | 1/1997 | Cinquin et al. |
| 5,600,303 A | 2/1997 | Husseiny et al. |
| 5,600,485 A | 2/1997 | Iwaki et al. |
| 5,600,700 A | 2/1997 | Krug et al. |
| 5,604,634 A | 2/1997 | Khoury et al. |
| 5,619,596 A | 4/1997 | Iwaki et al. |
| 5,625,192 A | 4/1997 | Oda et al. |
| 5,625,717 A | 4/1997 | Hashimoto et al. |
| 5,638,420 A | 6/1997 | Armistead |
| 5,642,393 A | 6/1997 | Krug et al. |
| 5,642,394 A | 6/1997 | Rothschild |
| 5,647,018 A | 7/1997 | Benjamin |
| 5,664,574 A | 9/1997 | Chance |
| 5,668,846 A | 9/1997 | Fox et al. |
| 5,680,525 A | 10/1997 | Sakai et al. |
| 5,684,565 A | 11/1997 | Oshida et al. |
| 5,692,028 A | 11/1997 | Geus et al. |
| 5,692,029 A | 11/1997 | Husseiny et al. |
| 5,692,446 A | 12/1997 | Becker et al. |
| 5,699,400 A | 12/1997 | Lee et al. |
| 5,703,921 A | 12/1997 | Fujita et al. |
| 5,706,816 A | 1/1998 | Mochizuki et al. |
| 5,726,449 A | 3/1998 | Yoshiike et al. |
| 5,739,539 A | 4/1998 | Wang et al. |
| 5,745,542 A | 4/1998 | Gordon et al. |
| 5,748,305 A | 5/1998 | Shimono et al. |
| 5,748,697 A | 5/1998 | Tam |
| 5,754,621 A | 5/1998 | Suzuki et al. |
| 5,756,875 A | 5/1998 | Parker et al. |
| 5,757,981 A | 5/1998 | Kawakubo |
| 5,761,334 A | 6/1998 | Nakajima et al. |
| 5,764,683 A | 6/1998 | Swift et al. |
| 5,764,719 A | 6/1998 | Noettling |
| 5,768,334 A | 6/1998 | Maitrejean et al. |
| 5,777,742 A | 7/1998 | Marron |
| 5,778,046 A | 7/1998 | Molloi et al. |
| 5,779,641 A | 7/1998 | Hatfield et al. |
| 5,784,429 A | 7/1998 | Arai |
| 5,786,597 A | 7/1998 | Lingren et al. |
| 5,787,145 A | 7/1998 | Geus |
| 5,794,788 A | 8/1998 | Massen |
| 5,796,802 A | 8/1998 | Gordon |
| 5,796,868 A | 8/1998 | Dutta-Choudhury |

| | | |
|---|---|---|
| 5,799,100 A | 8/1998 | Clarke et al. |
| 5,800,355 A | 9/1998 | Hasegawa |
| 5,802,133 A | 9/1998 | Kawai et al. |
| 5,809,171 A | 9/1998 | Neff et al. |
| 5,815,198 A | 9/1998 | Vachtsevanos et al. |
| 5,815,264 A | 9/1998 | Reed et al. |
| 5,828,722 A | 10/1998 | Ploetz et al. |
| 5,828,774 A | 10/1998 | Wang |
| 5,834,153 A | 11/1998 | Hasegawa et al. |
| 5,838,758 A | 11/1998 | Krug et al. |
| 5,838,759 A | 11/1998 | Armistead |
| 5,841,828 A | 11/1998 | Gordon et al. |
| 5,841,907 A | 11/1998 | Javidi et al. |
| 5,850,465 A | 12/1998 | Shimura et al. |
| 5,862,198 A | 1/1999 | Samarasekera et al. |
| 5,862,258 A | 1/1999 | Taylor |
| 5,864,598 A | 1/1999 | Hsieh et al. |
| 5,866,907 A | 2/1999 | Drukier et al. |
| 5,877,849 A | 3/1999 | Ramer et al. |
| 5,881,123 A | 3/1999 | Tam |
| 5,893,095 A | 4/1999 | Jain et al. |
| 5,894,345 A | 4/1999 | Takamoto et al. |
| 5,901,196 A | 5/1999 | Sauer et al. |
| 5,901,198 A | 5/1999 | Crawford et al. |
| 5,903,623 A | 5/1999 | Swift et al. |
| 5,909,285 A | 6/1999 | Beaty et al. |
| 5,909,477 A | 6/1999 | Crawford et al. |
| 5,910,765 A | 6/1999 | Slemon et al. |
| 5,910,973 A | 6/1999 | Grodzins |
| 5,911,139 A | 6/1999 | Jain et al. |
| 5,917,190 A | 6/1999 | Yodh et al. |
| 5,926,568 A | 7/1999 | Chaney et al. |
| 5,940,468 A | 8/1999 | Huang et al. |
| 5,943,388 A | 8/1999 | Tumer |
| 5,951,474 A | 9/1999 | Matsunaga et al. |
| 5,953,452 A | 9/1999 | Boone et al. |
| 5,960,104 A | 9/1999 | Conners et al. |
| 5,974,111 A | 10/1999 | Krug et al. |
| 5,978,440 A | 11/1999 | Kang et al. |
| 5,981,949 A | 11/1999 | Leahy et al. |
| 5,987,095 A | 11/1999 | Chapman et al. |
| 6,005,916 A | 12/1999 | Johnson et al. |
| 6,008,496 A | 12/1999 | Winefordner et al. |
| 6,009,142 A | 12/1999 | Sauer et al. |
| 6,011,620 A | 1/2000 | Sites et al. |
| 6,018,561 A | 1/2000 | Tam |
| 6,018,562 A | 1/2000 | Willson |
| 6,031,890 A | 2/2000 | Bermbach et al. |
| 6,035,014 A | 3/2000 | Hiraoglu et al. |
| 6,043,870 A | 3/2000 | Chen |
| 6,049,381 A | 4/2000 | Reintjes et al. |
| 6,057,761 A | 5/2000 | Yukl |
| 6,057,909 A | 5/2000 | Yahav et al. |
| 6,058,159 A | 5/2000 | Conway et al. |
| 6,060,677 A | 5/2000 | Ulrichsen et al. |
| 6,070,583 A | 6/2000 | Perelman et al. |
| 6,075,591 A | 6/2000 | Vokhmin |
| 6,075,880 A | 6/2000 | Kollhof et al. |
| 6,078,638 A | 6/2000 | Sauer et al. |
| 6,080,994 A | 6/2000 | Carrott et al. |
| 6,081,580 A | 6/2000 | Grodzins et al. |
| 6,084,939 A | 7/2000 | Tamura |
| 6,088,423 A | 7/2000 | Krug et al. |
| 6,094,472 A | 7/2000 | Smith |
| 6,097,427 A | 8/2000 | Dey et al. |
| 6,149,300 A | 11/2000 | Greenway et al. |
| 6,153,873 A | 11/2000 | Wolf |
| 6,155,179 A | 12/2000 | Aust et al. |
| 6,157,730 A | 12/2000 | Roever et al. |
| 6,163,403 A | 12/2000 | Carrott et al. |
| 6,175,417 B1 | 1/2001 | Do et al. |
| 6,175,613 B1 | 1/2001 | Boutenko et al. |
| 6,188,747 B1 | 2/2001 | Geus et al. |
| 6,195,413 B1 | 2/2001 | Geus et al. |
| 6,195,444 B1 | 2/2001 | Simanovsky et al. |
| 6,198,795 B1 | 3/2001 | Naumann et al. |
| 6,205,195 B1 | 3/2001 | Lanza |
| 6,205,243 B1 | 3/2001 | Migdal et al. |
| 6,218,943 B1 | 4/2001 | Ellenbogen |
| 6,222,902 B1 | 4/2001 | Lin et al. |
| 6,229,872 B1 | 5/2001 | Amos |
| 6,233,303 B1 | 5/2001 | Tam |
| 6,236,704 B1 | 5/2001 | Navab et al. |
| 6,236,708 B1 | 5/2001 | Lin et al. |
| 6,249,341 B1 | 6/2001 | Basiji et al. |
| 6,252,929 B1 | 6/2001 | Swift et al. |
| 6,256,370 B1 | 7/2001 | Yavuz |
| 6,256,404 B1 | 7/2001 | Gordon et al. |
| 6,263,044 B1 | 7/2001 | Joosten |
| 6,263,231 B1 | 7/2001 | Reitter |
| 6,272,204 B1 | 8/2001 | Amtower et al. |
| 6,272,233 B1 | 8/2001 | Takeo |
| 6,278,760 B1 | 8/2001 | Ogawa et al. |
| 6,288,974 B1 | 9/2001 | Nelson |
| 6,289,235 B1 | 9/2001 | Webber et al. |
| 6,292,260 B1 | 9/2001 | Lin et al. |
| 6,292,530 B1 | 9/2001 | Yavus et al. |
| 6,292,533 B1 | 9/2001 | Swift et al. |
| 6,324,245 B1 | 11/2001 | Tam |
| 6,353,673 B1 | 3/2002 | Shnitser et al. |
| 6,366,638 B1 | 4/2002 | Hsieg et al. |
| 6,370,222 B1 | 4/2002 | Cornick |
| 6,373,916 B1 | 4/2002 | Inoue et al. |
| 6,373,970 B1 | 4/2002 | Dong et al. |
| 6,381,297 B1 | 4/2002 | Hsieh |
| 6,388,788 B1 | 5/2002 | Harris et al. |
| 6,403,960 B1 | 6/2002 | Wellnitz et al. |
| 6,404,841 B1 | 6/2002 | Pforr et al. |
| 6,408,042 B1 | 6/2002 | Hsieh |
| 6,415,012 B1 | 7/2002 | Taguchi et al. |
| 6,418,184 B1 | 7/2002 | Wang et al. |
| 6,418,189 B1 | 7/2002 | Schafer |
| 6,424,692 B1 | 7/2002 | Suzuki |
| 6,442,288 B1 | 8/2002 | Haerer et al. |
| 6,445,765 B1 | 9/2002 | Frank et al. |
| 6,448,545 B1 | 9/2002 | Chen |
| 6,453,003 B1 | 9/2002 | Springer et al. |
| 6,459,755 B1 | 10/2002 | Li |
| 6,463,181 B2 | 10/2002 | Duarte |
| 6,473,489 B2 | 10/2002 | Bani-Hashemi et al. |
| 6,477,221 B1 | 11/2002 | Ning |
| 6,480,285 B1 | 11/2002 | Hill |
| 6,480,564 B1 | 11/2002 | Kim et al. |
| 6,483,894 B2 | 11/2002 | Hartick et al. |
| 6,487,307 B1 | 11/2002 | Hennessey et al. |
| 6,502,984 B2 | 1/2003 | Ogura et al. |
| 6,507,025 B1 | 1/2003 | Verbinski et al. |
| 6,507,278 B1 | 1/2003 | Brunetti et al. |
| 6,525,331 B1 | 2/2003 | Ngoi et al. |
| 6,526,120 B1 | 2/2003 | Gray et al. |
| 6,532,276 B1 | 3/2003 | Hartick et al. |
| 6,542,574 B2 | 4/2003 | Grodzins |
| 6,542,578 B2 | 4/2003 | Ries et al. |
| 6,542,579 B1 | 4/2003 | Takasawa |
| 6,542,580 B1 | 4/2003 | Carver et al. |
| 6,542,628 B1 | 4/2003 | Muller et al. |
| 6,549,683 B1 | 4/2003 | Bergeron et al. |
| 6,552,809 B1 | 4/2003 | Bergeron et al. |
| 6,559,769 B2 | 5/2003 | Anthony et al. |
| 6,570,177 B1 | 5/2003 | Struckhoff et al. |
| 6,570,708 B1 | 5/2003 | Bergeron et al. |
| 6,570,951 B1 | 5/2003 | Hsieh |
| 6,570,956 B1 | 5/2003 | Rhee et al. |
| 6,574,296 B2 | 6/2003 | Stierstorfer |
| 6,574,297 B2 | 6/2003 | Tam |
| 6,580,777 B1 | 6/2003 | Ueki et al. |

| Patent | Date | Name |
|---|---|---|
| 6,580,778 B2 | 6/2003 | Meder |
| 6,583,895 B1 | 6/2003 | Kuwahara et al. |
| 6,584,170 B2 | 6/2003 | Aust et al. |
| 6,586,193 B2 | 7/2003 | Yguerabide et al. |
| 6,587,575 B1 | 7/2003 | Windham et al. |
| 6,587,595 B1 | 7/2003 | Henkel et al. |
| 6,597,760 B2 | 7/2003 | Beneke et al. |
| 6,603,536 B1 | 8/2003 | Hasson et al. |
| 6,608,921 B1 | 8/2003 | Inoue et al. |
| 6,611,575 B1 | 8/2003 | Alyassin et al. |
| 6,618,466 B1 | 9/2003 | Ning |
| 6,621,887 B2 | 9/2003 | Albagli et al. |
| 6,621,888 B2 | 9/2003 | Grodzins et al. |
| 6,621,925 B1 | 9/2003 | Ohmori et al. |
| 6,628,982 B1 | 9/2003 | Thomas et al. |
| 6,628,983 B1 | 9/2003 | Gagnon |
| 6,654,443 B1 | 11/2003 | Hoffman |
| 6,663,280 B2 | 12/2003 | Doenges |
| 6,665,373 B1 | 12/2003 | Kotowski et al. |
| 6,707,879 B2 | 3/2004 | McClelland et al. |
| 6,714,623 B2 | 3/2004 | Sako et al. |
| 6,721,387 B1 | 4/2004 | Naidu et al. |
| 6,721,391 B2 | 4/2004 | McClelland et al. |
| 6,724,922 B1 | 4/2004 | Vilsmeier |
| 6,731,819 B1 | 5/2004 | Fukushima et al. |
| 6,735,274 B1 | 5/2004 | Zahavi et al. |
| 6,735,279 B1 | 5/2004 | Jacobs et al. |
| 6,738,450 B1 | 5/2004 | Barford |
| 6,744,909 B1 | 6/2004 | Kostrzewski et al. |
| 6,746,864 B1 | 6/2004 | McNeil et al. |
| 6,751,349 B2 | 6/2004 | Matama |
| 6,754,374 B1 | 6/2004 | Miller et al. |
| 6,763,148 B1 | 7/2004 | Sternberg et al. |
| 6,785,410 B2 | 8/2004 | Vining et al. |
| 6,801,647 B1 | 10/2004 | Arakawa |
| 6,803,997 B2 | 10/2004 | Stanek |
| 6,804,412 B1 | 10/2004 | Wilkinson |
| 6,813,395 B1 | 11/2004 | Kinjo |
| 6,825,854 B1 | 11/2004 | Beneke et al. |
| 6,837,422 B1 | 1/2005 | Meder |
| 6,839,403 B1 | 1/2005 | Kotowski et al. |
| 6,839,406 B2 | 1/2005 | Ries et al. |
| 6,843,599 B2 | 1/2005 | Le et al. |
| 6,856,272 B2 | 2/2005 | Levitan et al. |
| 6,865,287 B1 | 3/2005 | Beneke |
| 6,865,509 B1 | 3/2005 | Hsiung et al |
| 6,868,138 B2 | 3/2005 | Clinthorne et al. |
| 6,873,261 B2 | 3/2005 | Anthony et al. |
| 6,876,322 B2 | 4/2005 | Keller |
| 6,895,072 B2 | 5/2005 | Schrock et al. |
| 6,895,338 B2 | 5/2005 | Hsiung et al. |
| 6,899,540 B1 | 5/2005 | Neiderman et al. |
| 6,918,541 B2 | 7/2005 | Knowles et al. |
| 6,928,141 B2 | 8/2005 | Carver et al. |
| 6,936,828 B2 | 8/2005 | Saccomanno |
| 6,938,488 B2 * | 9/2005 | Diaz et al. .................... 73/597 |
| 6,940,943 B2 | 9/2005 | Claus et al. |
| 6,950,492 B2 | 9/2005 | Besson |
| 6,952,163 B2 | 10/2005 | Huey et al. |
| 6,970,531 B2 | 11/2005 | Eberhard et al. |
| 6,980,681 B1 | 12/2005 | Hsieh |
| 6,982,643 B2 | 1/2006 | Garfinkle |
| 6,990,171 B2 | 1/2006 | Toth et al. |
| 7,000,827 B2 | 2/2006 | Meder |
| 7,012,256 B1 | 3/2006 | Roos et al. |
| 7,020,241 B2 | 3/2006 | Beneke et al. |
| 7,043,474 B2 | 5/2006 | Mojsilovic et al. |
| 7,045,787 B1 | 5/2006 | Verbinski et al. |
| 7,046,761 B2 | 5/2006 | Ellenbogen et al. |
| 7,050,616 B2 | 5/2006 | Hsieh et al. |
| 7,062,074 B1 | 6/2006 | Beneke |
| 7,065,175 B2 | 6/2006 | Green |
| 7,068,751 B2 | 6/2006 | Toth et al. |
| 7,092,485 B2 | 8/2006 | Kravis |
| 7,098,461 B2 | 8/2006 | Endo |
| 7,099,004 B2 | 8/2006 | Masten |
| 7,099,432 B2 | 8/2006 | Ichihara et al. |
| 7,100,165 B2 | 8/2006 | Eldridge et al. |
| 7,103,137 B2 | 9/2006 | Seppi et al. |
| 7,105,828 B2 | 9/2006 | Unger et al. |
| 7,116,749 B2 | 10/2006 | Besson |
| 7,130,456 B2 | 10/2006 | Hillmann |
| 7,136,716 B2 | 11/2006 | Hsiung et al. |
| 7,139,406 B2 | 11/2006 | McClelland et al. |
| 7,142,633 B2 | 11/2006 | Eberhard et al. |
| 7,154,650 B2 | 12/2006 | Lettington |
| 7,164,750 B2 | 1/2007 | Nabors et al. |
| 7,183,906 B2 | 2/2007 | Zanovitch et al. |
| 7,193,515 B1 | 3/2007 | Roberts et al. |
| 7,212,113 B2 | 5/2007 | Zanovitch |
| 7,212,661 B2 | 5/2007 | Samara et |
| 7,233,682 B2 | 6/2007 | Levine |
| 7,244,941 B2 | 7/2007 | Roos et al. |
| 7,257,189 B2 | 8/2007 | Modica et al. |
| 2001/0016030 A1 | 8/2001 | Nicolas et al. |
| 2001/0021013 A1 | 9/2001 | Hecht et al. |
| 2001/0021244 A1 | 9/2001 | Suzuki et al. |
| 2001/0028696 A1 | 10/2001 | Yamada et al. |
| 2001/0033636 A1 | 10/2001 | Hartick et al. |
| 2001/0038681 A1 | 11/2001 | Stanton et al. |
| 2001/0038705 A1 | 11/2001 | Rubbert et al. |
| 2001/0038707 A1 | 11/2001 | Ohara |
| 2001/0048734 A1 | 12/2001 | Uppaluri et al. |
| 2001/0053197 A1 | 12/2001 | Murayama et al. |
| 2002/0001366 A1 | 1/2002 | Tamura et al. |
| 2002/0015475 A1 | 2/2002 | Matsumoto et al. |
| 2002/0016546 A1 | 2/2002 | Cerofolini |
| 2002/0017620 A1 | 2/2002 | Oomori et al. |
| 2002/0018199 A1 | 2/2002 | Blumenfeld et al. |
| 2002/0024016 A1 | 2/2002 | Endo |
| 2002/0027970 A1 | 3/2002 | Chapman et al. |
| 2002/0028994 A1 | 3/2002 | Kamiyama |
| 2002/0031246 A1 | 3/2002 | Kawano |
| 2002/0037068 A1 | 3/2002 | Oikawa |
| 2002/0044691 A1 | 4/2002 | Matsugu |
| 2002/0054694 A1 | 5/2002 | Vachtsevanos et al. |
| 2002/0067259 A1 | 6/2002 | Fufidio et al. |
| 2002/0067793 A1 | 6/2002 | Stierstorfer |
| 2002/0085046 A1 | 7/2002 | Furuta et al. |
| 2002/0088952 A1 | 7/2002 | Rao et al. |
| 2002/0094062 A1 | 7/2002 | Dolazza et al. |
| 2002/0094119 A1 | 7/2002 | Sahadevan |
| 2002/0098518 A1 | 7/2002 | Levinson |
| 2002/0106052 A1 | 8/2002 | Menhardt |
| 2002/0122528 A1 | 9/2002 | Besson |
| 2002/0124664 A1 | 9/2002 | Call et al. |
| 2002/0126800 A1 | 9/2002 | Matsumoto et al. |
| 2002/0127586 A1 | 9/2002 | Mortensen |
| 2002/0141625 A1 | 10/2002 | Nelson |
| 2002/0150200 A1 | 10/2002 | Zonneveld |
| 2002/0161534 A1 | 10/2002 | Adler et al. |
| 2002/0168083 A1 | 11/2002 | Garms et al. |
| 2002/0168657 A1 | 11/2002 | Chen et al. |
| 2002/0172324 A1 | 11/2002 | Ellengogen |
| 2002/0172409 A1 | 11/2002 | Saito et al. |
| 2002/0175921 A1 | 11/2002 | Xu et al. |
| 2002/0176534 A1 | 11/2002 | Meder |
| 2002/0186862 A1 | 12/2002 | McClelland et al. |
| 2002/0188197 A1 | 12/2002 | Bishop et al. |
| 2002/0191209 A1 | 12/2002 | Yasumaru |
| 2003/0012420 A1 | 1/2003 | Verwoerd et al. |
| 2003/0023592 A1 | 1/2003 | Modica et al. |
| 2003/0024315 A1 | 2/2003 | Merkel et al. |
| 2003/0031289 A1 | 2/2003 | Hsieh |
| 2003/0031291 A1 | 2/2003 | Yamamoto et al. |
| 2003/0036006 A1 | 2/2003 | Feke et al. |

| | | | | | | |
|---|---|---|---|---|---|---|
| 2003/0038945 A1 | 2/2003 | Mahner | | 2004/0253660 A1 | 12/2004 | Gibbs et al. |
| 2003/0072414 A1 | 4/2003 | Sakaida | | 2004/0258198 A1 | 12/2004 | Carver et al. |
| 2003/0072418 A1 | 4/2003 | Albagli et al. | | 2004/0258202 A1 | 12/2004 | Wernick et al. |
| 2003/0072484 A1 | 4/2003 | Kokko et al. | | 2004/0263379 A1 | 12/2004 | Keller |
| 2003/0076924 A1 | 4/2003 | Mario et al. | | 2004/0264624 A1 | 12/2004 | Tanaka et al. |
| 2003/0081720 A1 | 5/2003 | Swift et al. | | 2004/0264648 A1 | 12/2004 | Claus et al. |
| 2003/0081859 A1 | 5/2003 | Kasutani | | 2004/0265175 A1 | 12/2004 | Witty et al. |
| 2003/0082516 A1 | 5/2003 | Straus | | 2005/0008119 A1 | 1/2005 | McClelland et al. |
| 2003/0085348 A1 | 5/2003 | Megerle | | 2005/0008203 A1 | 1/2005 | Dixon |
| 2003/0085353 A1 | 5/2003 | Almogy et al. | | 2005/0017181 A1 | 1/2005 | Kearfott et al. |
| 2003/0091145 A1 | 5/2003 | Mohr et al. | | 2005/0018812 A1 | 1/2005 | Wolfs |
| 2003/0095633 A1 | 5/2003 | Van Woezik | | 2005/0025280 A1 | 2/2005 | Schulte |
| 2003/0095692 A1 | 5/2003 | Mundy et al. | | 2005/0025350 A1 | 2/2005 | Engelbart et al. |
| 2003/0128812 A1* | 7/2003 | Appleby et al. ............. 378/147 | | 2005/0031069 A1 | 2/2005 | Kaucic et al. |
| 2003/0138147 A1 | 7/2003 | Ongkojoyo | | 2005/0053307 A1 | 3/2005 | Nose et al. |
| 2003/0148393 A1 | 8/2003 | Woodbury et al. | | 2005/0057354 A1 | 3/2005 | Jenkins et al. |
| 2003/0149346 A1 | 8/2003 | Arnone et al. | | 2005/0058242 A1 | 3/2005 | Peschmann |
| 2003/0165213 A1 | 9/2003 | Maglich | | 2005/0058350 A1 | 3/2005 | Dugan et al. |
| 2003/0179853 A1 | 9/2003 | Amemiya et al. | | 2005/0061955 A1 | 3/2005 | Endo |
| 2003/0194121 A1 | 10/2003 | Eberhard et al. | | 2005/0069085 A1 | 3/2005 | Lewis |
| 2003/0205676 A1 | 11/2003 | Nelson et al. | | 2005/0074088 A1 | 4/2005 | Ichihara et al. |
| 2003/0206649 A1 | 11/2003 | Moshe | | 2005/0085721 A1 | 4/2005 | Fauver et al. |
| 2003/0210139 A1 | 11/2003 | Brooks et al. | | 2005/0094856 A1 | 5/2005 | Warren |
| 2003/0215051 A1 | 11/2003 | Suzuki | | 2005/0098728 A1 | 5/2005 | Alfano et al. |
| 2003/0215143 A1* | 11/2003 | Zakrzewski et al. ......... 382/190 | | 2005/0105680 A1 | 5/2005 | Nabors et al. |
| 2003/0231788 A1 | 12/2003 | Yukhin et al. | | 2005/0110672 A1 | 5/2005 | Cardiasmenos et al. |
| 2003/0231791 A1 | 12/2003 | Torre-Bueno et al. | | 2005/0111618 A1 | 5/2005 | Sommer, Jr. et al. |
| 2004/0012853 A1 | 1/2004 | Garcia et al. | | 2005/0113961 A1 | 5/2005 | Sabol et al. |
| 2004/0013239 A1 | 1/2004 | Gregerson et al. | | 2005/0117693 A1 | 6/2005 | Miyano |
| 2004/0016271 A1 | 1/2004 | Shah et al. | | 2005/0117700 A1 | 6/2005 | Peschmann |
| 2004/0017882 A1 | 1/2004 | Misawa et al. | | 2005/0123093 A1 | 6/2005 | Lawaczeck et al. |
| 2004/0017883 A1 | 1/2004 | Takagi et al. | | 2005/0123174 A1 | 6/2005 | Gorsky et al. |
| 2004/0017888 A1 | 1/2004 | Seppi et al. | | 2005/0128069 A1 | 6/2005 | Skatter |
| 2004/0017935 A1 | 1/2004 | Avinash et al. | | 2005/0133708 A1 | 6/2005 | Eberhard et al. |
| 2004/0022425 A1 | 2/2004 | Avinash et al. | | 2005/0147199 A1 | 7/2005 | Dunham et al. |
| 2004/0027127 A1 | 2/2004 | Mills | | 2005/0153356 A1 | 7/2005 | Okawa et al. |
| 2004/0037462 A1 | 2/2004 | Lewis et al. | | 2005/0163354 A1 | 7/2005 | Ziegler |
| 2004/0041082 A1 | 3/2004 | Harmon | | 2005/0173284 A1 | 8/2005 | Ambrefe, Jr. |
| 2004/0051030 A1 | 3/2004 | Olszak et al. | | 2005/0189412 A1 | 9/2005 | Hudnut et al. |
| 2004/0062342 A1 | 4/2004 | Cahill | | 2005/0190882 A1 | 9/2005 | McGuire |
| 2004/0062349 A1 | 4/2004 | Schuster | | 2005/0206514 A1 | 9/2005 | Zanovitch et al. |
| 2004/0062351 A1 | 4/2004 | Yoshioka | | 2005/0207655 A1 | 9/2005 | Chopra et al. |
| 2004/0066882 A1 | 4/2004 | Eberhard et al. | | 2005/0212913 A1 | 9/2005 | Richter |
| 2004/0066884 A1 | 4/2004 | Claus et al. | | 2005/0219523 A1 | 10/2005 | Onuma et al. |
| 2004/0066890 A1 | 4/2004 | Dalmijn et al. | | 2005/0220264 A1 | 10/2005 | Homegger |
| 2004/0075058 A1 | 4/2004 | Blevis et al. | | 2005/0226375 A1 | 10/2005 | Eberhard et al. |
| 2004/0080315 A1 | 4/2004 | Beevor et al. | | 2005/0240858 A1* | 10/2005 | Croft et al. .................. 715/500 |
| 2004/0082846 A1 | 4/2004 | Johnson et al. | | 2005/0248450 A1 | 11/2005 | Zanovitch |
| 2004/0083958 A1 | 5/2004 | Saidman et al. | | 2005/0249416 A1 | 11/2005 | Leue et al. |
| 2004/0086075 A1 | 5/2004 | Hein et al. | | 2005/0251397 A1 | 11/2005 | Zanovitch et al. |
| 2004/0086160 A1 | 5/2004 | Zimmermann | | 2005/0251398 A1 | 11/2005 | Zanovitch et al. |
| 2004/0087844 A1 | 5/2004 | Yen | | 2005/0259868 A1 | 11/2005 | Sones |
| 2004/0102700 A1 | 5/2004 | Asafusa | | 2005/0265517 A1 | 12/2005 | Gary |
| 2004/0109231 A1 | 6/2004 | Haisch et al. | | 2005/0271184 A1 | 12/2005 | Ovadia |
| 2004/0120857 A1 | 6/2004 | Smith et al. | | 2005/0275831 A1 | 12/2005 | Silver |
| 2004/0134986 A1 | 7/2004 | Studer et al. | | 2005/0276443 A1 | 12/2005 | Slamani et al. |
| 2004/0141056 A1 | 7/2004 | Izumi et al. | | 2005/0279936 A1 | 12/2005 | Litman et al. |
| 2004/0142386 A1 | 7/2004 | Rigler et al. | | 2005/0283079 A1 | 12/2005 | Steen et al. |
| 2004/0160599 A1 | 8/2004 | Hamamatsu et al. | | 2006/0000911 A1 | 1/2006 | Stekel |
| 2004/0161073 A1 | 8/2004 | Nokita | | 2006/0002504 A1 | 1/2006 | De Man et al. |
| 2004/0175041 A1 | 9/2004 | Miller | | 2006/0008054 A1 | 1/2006 | Ohara |
| 2004/0176677 A1 | 9/2004 | Hwu et al. | | 2006/0009269 A1 | 1/2006 | Hoskinson et al. |
| 2004/0212492 A1 | 10/2004 | Boesch et al. | | 2006/0013455 A1 | 1/2006 | Watson et al. |
| 2004/0213377 A1 | 10/2004 | Endo | | 2006/0013464 A1 | 1/2006 | Ramsay et al. |
| 2004/0213600 A1 | 10/2004 | Watanabe et al. | | 2006/0017605 A1 | 1/2006 | Lovberg et al. |
| 2004/0218729 A1 | 11/2004 | Xue et al. | | 2006/0018434 A1 | 1/2006 | Jacobs et al. |
| 2004/0225222 A1 | 11/2004 | Zeng et al. | | 2006/0018517 A1 | 1/2006 | Chen et al. |
| 2004/0236520 A1 | 11/2004 | Williams et al. | | 2006/0019409 A1 | 1/2006 | Nelson et al. |
| 2004/0240612 A1 | 12/2004 | Suzuki | | 2006/0034503 A1 | 2/2006 | Shimayama |
| 2004/0247071 A1 | 12/2004 | Dafni | | 2006/0036167 A1 | 2/2006 | Shina |
| 2004/0252171 A1 | 12/2004 | Hashimoto et al. | | 2006/0045235 A1 | 3/2006 | Bruder et al. |
| 2004/0252024 A1 | 12/2004 | Huey et al. | | 2006/0045323 A1 | 3/2006 | Ateya |
| 2004/0252870 A1 | 12/2004 | Reeves et al. | | 2006/0064246 A1 | 3/2006 | Medberry et al. |

| | | | |
|---|---|---|---|
| 2006/0065844 A1 | 3/2006 | Zelakiewicz et al. | |
| 2006/0072702 A1 | 4/2006 | Chapman | |
| 2006/0083418 A1 | 4/2006 | Watson et al. | |
| 2006/0084872 A1 | 4/2006 | Ichikawa et al. | |
| 2006/0086794 A1 | 4/2006 | Knowles et al. | |
| 2006/0093088 A1 | 5/2006 | Sowerby et al. | |
| 2006/0098773 A1 | 5/2006 | Peschmann | |
| 2006/0098866 A1 | 5/2006 | Whitson et al. | |
| 2006/0115109 A1 | 6/2006 | Whitson et al. | |
| 2006/0116566 A1 | 6/2006 | Bruijns | |
| 2006/0119837 A1 | 6/2006 | Raguin et al. | |
| 2006/0133650 A1 | 6/2006 | Xie et al. | |
| 2006/0133659 A1 | 6/2006 | Hammond | |
| 2006/0142662 A1 | 6/2006 | Van Beek | |
| 2006/0142984 A1 | 6/2006 | Weese et al. | |
| 2006/0173268 A1 | 8/2006 | Mullick et al. | |
| 2006/0176062 A1 | 8/2006 | Yang et al. | |
| 2006/0203960 A1 | 9/2006 | Schlomka et al. | |
| 2006/0204080 A1 | 9/2006 | Sones et al. | |
| 2006/0215811 A1 | 9/2006 | Modica et al. | |
| 2006/0255929 A1 | 11/2006 | Zanovitch et al. | |
| 2006/0262902 A1 | 11/2006 | Wattenburg | |
| 2006/0269135 A1 | 11/2006 | Ramsay et al. | |
| 2006/0273257 A1 | 12/2006 | Roos et al. | |
| 2006/0274916 A1 | 12/2006 | Chan et al. | |
| 2006/0282886 A1 | 12/2006 | Gaug | |
| 2007/0003122 A1 | 1/2007 | Sirohey et al. | |
| 2007/0058037 A1 | 3/2007 | Bergeron et al. | |
| 2007/0147585 A1 | 6/2007 | Eilbert et al. | |
| 2007/0168467 A1 | 7/2007 | Hu et al. | |
| 2007/0195994 A1 | 8/2007 | McClelland et al. | |
| 2007/0200566 A1 | 8/2007 | Clark et al. | |
| 2007/0206719 A1 | 9/2007 | Suryanarayanan et al. | |
| 2007/0210921 A1 | 9/2007 | Volpi et al. | |
| 2008/0236275 A1 | 10/2008 | Breed et al. | |
| 2008/0260097 A1 * | 10/2008 | Anwar et al. | 378/57 |

FOREIGN PATENT DOCUMENTS

| | | |
|---|---|---|
| CA | 2319958 | 9/2000 |
| CA | 2574402 | 1/2006 |
| EP | 0 577 380 A1 | 1/1994 |
| WO | WO 02/082290 A1 | 10/2002 |
| WO | WO 03/069498 A1 | 8/2003 |
| WO | WO 03/107113 A3 | 12/2003 |
| WO | PCT/CA2005/000716 | 5/2005 |
| WO | WO 2005/086616 A2 | 9/2005 |
| WO | PCT/CA2005/001930 | 12/2005 |
| WO | PCT/CA2006/000655 | 4/2006 |
| WO | PCT/CA2006/000655 | 8/2006 |
| WO | PCT/CA2006/000751 | 8/2006 |
| WO | WO 2006/119603 A1 | 11/2006 |
| WO | PCT/CA2007/001749 | 1/2007 |
| WO | PCT/CA2007/000779 | 8/2007 |
| WO | PCT/CA2007/000840 | 8/2007 |
| WO | PCT/CA2007/001658 | 9/2007 |
| WO | PCT/CA2007/001297 | 11/2007 |
| WO | PCT/CA2007/001298 | 11/2007 |
| WO | PCT/CA2008/000275 | 2/2008 |

OTHER PUBLICATIONS

Airport Magazine, Solutions, Products, Services, vol. 7, Mar. 2006, selected pages.

H.J. Caufield and W.T. Maloney, Improved discrimination in optical character recognition, 1969, Appl. Opt., 8, p. 2354.

Mahalanobis, A. et al., Minimum average correlation energy filters, Sep. 1, 1987, Appl. Opt. 26 No. 17, pp. 3633-3640.

Joseph L. Horner et al., Phase-only matched filtering, Mar. 15, 1994, Appl. Opt. vol. 23 No. 6, pp. 812-816.

Benjamin R., Object-based 3D X-ray imaging for second-line security screening, 1995, Conf. Publ. No. 408, Londonn, UK: IEE, pp. 310-313.

Andre Morin et al., Optical character recognition (OCR) in uncontrolled environnments using optical correlators, 1999, SPIE Int., pp. 346-356.

PinPoint TM Threat Identification Software dated Jul. 25, 2005 of URL: http://www.guardiantechintl.com/security.php?npage=pinpoint, 4 pages.

Gregor McDonald, Fast Pattern Recognition, QinetiQ.

Secure Flight passenger screening program, http://www.globalsecurity.org/securiy/systems/passenger_screen.htm, 6 pages.

Security technology overview: Advanced vehicle verification & threat identification, www.optosecurity.com and www.extremeCTV.com, 1 page.

B.V.K. Vijaya Kumar et al., Spatial Frequency Domain Image Processing for Biometric Recognition, 2002, pp. I-53-I-56, vol. 1, IEEE ICIP, Pittsburgh, PA, USA.

International Preliminary Report on Patentability mailed on Oct. 15, 2009 in connection with International Patent Application PCT/CA2008/000275.

Office Action mailed on Jul. 2, 2009 in connection with U.S. Appl. No. 11/431,627.

Office Action Issued on Dec. 2, 2008 in connection with Canadian Patent Application 2,546,296.

Office Action Issued on Jun. 29, 2009 in connection with Canadian Patent Application 2,651,131.

United States Statutory Invention Registration No. H2110H (Newman) published on Oct. 5, 2004.

* cited by examiner

METHOD AND SYSTEM FOR SCREENING CARGO CONTAINERS

CROSS-REFERENCES TO RELATED APPLICATIONS

This application is a continuation-in-part application of international PCT patent application serial number PCT/CA2005/000716 filed May 11, 2005 designating the United States. The contents of the above referenced application are incorporated herein by reference.

FIELD OF THE INVENTION

The present invention relates generally to container contents verification and, more particularly, to methods, systems and devices for verifying the contents of containers, preferably large shipping containers.

BACKGROUND

Everyday, thousands of cargo containers arrive at various destinations around the world, be it at airports, train stations, ports, buildings and other public or private venues. The containers are used to carry a broad range of items including, but not limited to, vehicles, food, livestock and clothing.

The global economy necessitates that cargo containers for import and export trade be moved in a manner that assures a nation's citizens and the foreign trading and business community that the risk experienced will be at acceptable and predictable levels. As such assuring a safe and efficient flow of cargo containers is critical to a vibrant global economy.

The basic tool today for monitoring cargo containers is the manifest. Typically, the cargo manifest describes, amongst other things, the objects expected to be present in the cargo container. The cargo manifest is the basis of commercial agreements, e.g., assuring that what is shipped is what ultimately arrives at its destination. The cargo manifest is typically also the basis of monitoring hazardous cargo stowage, proper freight rate assessments and assessing customs duties. The United States government has recently implemented a program called CSI (Container Security Initiative) which makes use of the manifest of selected containers at foreign ports before these ones are shipped to the U.S.

A first deficiency associated with the use of a cargo manifest alone for assessing the content of a cargo container is the possibility of cargo theft. Cargo theft is the removal of one or more items from the cargo container after the manifest has been created. As such, the content of the cargo container at the departure location is different from the content of the cargo container at the arrival location. A method typically used for remedying this deficiency is to close the cargo container with a seal or with "smart" door sensors. "Smart" door sensors are typically adapted to detect changes in light intensity or other changes in the internal environment of the container. It follows therefore, in theory, that if the seal of a cargo container is not broken or if no change in light intensity or in the internal environment of the container was detected, the content of that cargo container should match the expected content of the cargo container as it is expressed in the manifest.

A second deficiency associated with the use of a cargo manifest is the possibility of manifest fraud. Manifest fraud includes the introduction of illicit cargo (arms, drugs, people, counterfeit objects) in a cargo container after the manifest has been created or the omission from the manifest of already present cargo. As such, the actual content of the container at the departure location is different from that expressed in the manifest. As can be readily appreciated, the above-described deficiency is not corrected by applying a seal to the cargo container or by the use of "smart" door sensors.

The use of a cargo manifest in a non-complex environment in which there is no possibility of fraud or deceitful actions may be adequate, but in complex environments, its use becomes increasingly inadequate and insecure. As such, even if a cargo container is associated to a manifest and is sealed, its actual content may be different from that expressed by the manifest. For that reason, verification of the content of a cargo container is required to ensure that the contents correspond to the manifest.

In practice, such verification is performed manually by having a customs agent, or a port official, break the seal of the cargo container and make a visual inspection of its content on the basis of the manifest. As can be readily appreciated, such a procedure is time consuming and costly both from a human resource perspective (since customs or security agents must be hired to perform this inspection) as well as from an economic perspective, since the cargo containers are delayed in transit waiting to be screened. For that reason, not all cargo containers are screened but rather a small percentage of the containers (about 4% in 2005) are screened in the manner described above. The manner in which cargo containers are selected for screening varies from random selection to selections based on risk factors (origin, type of shipment, destination, etc. . . . ). However, a large number of cargo containers go unscreened leaving a loophole available for smuggling (of drugs, arms and people), manifest fraud and other unlawful activities. As terrorism and smuggling increase, the potential problems that such a loophole allows are significant not only from an economic standpoint but also from a national security perspective.

A proposed solution to the above is described in U.S. Pat. No. 6,370,222, issued Apr. 9, 2002 to Cornick, Jr. and assigned to CCVS, LLC, Annandale Va. (US). The contents of the above noted patent are incorporated herein by reference. More specifically, U.S. Pat. No. 6,370,222 describes a method and system for verifying the contents of a cargo container which includes acquiring at the departure port at least one image of the cargo container and of the contents of the cargo container and storing the image with a manifest associated with the cargo container. The manifest is sent to another location, say to the arrival port, and, at the other location, selectively, a second image of the contents of the cargo container is acquired and compared with the original image stored with the manifest associated with the cargo container.

A deficiency with the above described solution is that it requires obtaining two (2) images of the cargo container—one at the departure port and one at the arrival port. As such, the above-described system requires that both the departure and arrival locations be equipped with similar equipment and imaging capabilities. Since the departure and arrival locations may be located in different countries, providing this type of coordination may be prohibitively complex and is impractical. Another deficiency associated to the above-described method is that it generally requires a human operator to effect a comparison between the images and the manifest which is time consuming and costly.

Consequently, there is a need in the industry for providing a method and system for use in screening cargo containers to verify the contents thereof that alleviate at least in part the deficiencies of the prior art.

SUMMARY OF THE INVENTION

In accordance with a broad aspect, the invention provides a system for screening cargo containers. The system comprises an image generation device suitable for generating an image signal associated with a cargo container, the image signal conveying information related to the contents of the cargo container. The system also comprises an apparatus including a first input for receiving the image signal associated with the cargo container, a second input for receiving a list of objects conveying objects expected to be present in the cargo container and a processing unit. The processing unit is operative for processing the image signal associated with the cargo container in combination with the list of objects and a group of target images associated with objects to derive mismatch information data. The mismatch information data conveys at least one distinction between the list of objects and the information related to the contents of the cargo container conveyed by the image signal. The apparatus includes an output for releasing information conveying the mismatch information data. The system includes an output module for conveying to a user of the system information derived at least in part on the basis of the mismatch information data.

In accordance with a specific implementation, list of objects is a first list of objects. The processing unit processes the image signal associated with the cargo container in combination with the group of target images associated with objects to detect a presence of at least one object in the cargo container. The processing unit then generates a second list of objects conveying objects whose presence in the container was detected. The processing unit then compares the second list of objects with the first list of objects to derive the mismatch information data. The mismatch information data may convey an object present in the first list of objects but absent from the second list of objects. Alternatively, the mismatch information data may convey an object present in the second list of objects (i.e. detected in the container) but absent from the first list of objects.

In a specific implementation, the first list of objects is derived from a manifest associated with the container. In a specific implementation, the cargo container is associated to a cargo identifier data element and the processing unit processes the cargo identifier data element in combination with a cargo container database including a plurality of manifest to identify a manifest associated with the cargo container.

In accordance with a specific implementation, the processing unit processes a database of target images on the basis of the first list of objects to derive the group of target images, the group of target images being indicative of a subset of the database of target images. Advantageously, this allows reducing the number of target images in the database that are processed in combination with the image signal.

In a specific implementation, the output module includes a display screen for conveying to a user of the system information derived at least in part on the basis of the mismatch information in visual format. Alternatively, the output module includes an audio output for conveying to a user of the system information derived at least in part on the basis of the mismatch information in audio format.

In a specific implementation, the processing unit is operative for generating log information data elements conveying the mismatch information and storing the log information data elements on a computer readable storage medium. The log information may include a time stamp data element indicating timing information associated to the cargo container or any other suitable type of information. The timing information may be the time at which the cargo container arrived at a certain location, the time at which the cargo container was screened and/or the time at which the mismatch information was generated.

In a specific example of implementation, the apparatus is operative for effecting a correlation operation between data derived from the image signal and at least one target image in the group of target images. The correlation operation may be effected optically, by using an optical correlator, or digitally using a programmed digital computer or dedicated hardware. In an alternative example of implementation, the comparisons between the image signal associated with the cargo container and at least some images in the plurality of target images is effected using any suitable image processing algorithm.

In a specific example of implementation, the image generation device uses penetrating radiation or emitted radiation to generate the image associated with the cargo container. Examples include, but are not limited to, x-ray, gamma ray, computed tomography (CT scan), thermal imaging and millimeter wave. The image signal generated may also be in any suitable format such as for example, VGA, SVGA, XGA, JPEG, GIF, TIFF and bitmap amongst others. The image signal associated with the cargo container is a two-dimensional image or a three-dimensional image.

In accordance with a specific implementation, the group of target images includes data elements indicative of Fourier transforms of target images and the processing unit includes an optical correlator. The optical correlator is operative for processing the image signal associated with the cargo container to derive a first Fourier transform data element indicative of a Fourier transform of the image signal associated with the cargo container. The optical correlator also computes a correlation operation between the first Fourier transform data element and the Fourier transform of at least one target image to detect a presence of the at least one target object in the cargo container.

In accordance with another broad aspect, the invention provides a method for screening a cargo container. The method comprises receiving an image signal associated with the cargo container, the image signal conveying information related to contents of the cargo container. The method also comprises receiving a list of objects conveying objects expected to be present in the cargo container. The method also comprises processing the image signal associated with the cargo container in combination with the list of objects and with a group of target images associated with objects to derive mismatch information data. The mismatch information data conveys at least one distinction between the list of objects and the information related to the contents of the cargo container conveyed by the image signal. The method also includes releasing information conveying the mismatch information data.

In accordance with another broad aspect, the invention provides and apparatus suitable for screening cargo containers in accordance with the above described method.

In accordance with another broad aspect, the invention provides a computer readable storage medium including a program element suitable for execution by a computing apparatus for screening cargo containers, the computing apparatus comprising a memory unit and a processor operatively connected to the memory unit. The program element when executing on the processor is operative for receiving an image signal associated with the cargo container, the image signal conveying information related to the contents of the cargo container. The program element, when executing on the processor, is also operative for receiving a first list of objects conveying objects expected to be present in the cargo container. The program element, when executing on the processor, is also operative for causing the image signal associated with the cargo container to be processed in combination with a group of target images associated with objects to detect a presence of at least one object in the container. The program element when executing on the processor is also operative for generating a second list of objects, the second list of objects conveying objects whose presence in the container was detected. The program element, when executing on the processor, is also operative for comparing the second list of objects with the first list of objects to derive mismatch information data conveying at least one distinction between the first list of objects and the second list of objects. The program element when executing on the processor is operative for releasing information conveying the mismatch information data.

In accordance with yet another broad aspect, the invention provides an apparatus for screening a cargo container. The apparatus comprises means for receiving an image signal associated with the cargo container, the image signal conveying information related to the contents of the cargo container. The apparatus also comprises means for receiving a list of objects conveying objects expected to be present in the cargo container. The apparatus also comprises means for processing the image signal associated with the cargo container in combination with the list of objects and with a group of target images associated with objects to derive mismatch information data. The mismatch information data conveys at least one distinction between the first list of objects and the information related to the contents of the cargo container conveyed by the image signal. The apparatus also provides means for releasing information conveying the mismatch information data.

In accordance with yet another broad aspect, the invention provides an apparatus for authenticating the contents of a cargo container. The apparatus comprises a first input for receiving data conveying graphic information regarding the contents of the container and a second input for receiving data conveying an expected content of the container. The apparatus also comprises an optical correlator and a processing unit. The optical correlator is operative for processing the graphic information to detect depictions of one or more objects in the container. The processing unit is operative for generating a list of objects detected in the container by the optical correlator and for processing the list of objects detected in the container in combination with the data conveying an expected content of the container to derive mismatch information data. The mismatch information data conveys at least one distinction between the list of objects detected in the container and the data conveying an expected content of the container. The apparatus also includes an output for releasing a signal conveying the mismatch information data.

For the purpose of this specification, the expression "cargo container" is used to broadly describe an enclosures for storing cargo such as would be used, for example, in a ship, train, truck, van, or an other suitable type of cargo container. The expression "cargo container" extends to a receptacle for the storage or transportation of goods, and includes freight pallets as well as vehicles, whether motorized or drawn, such as automobiles, the cab and trailer of a truck, railroad cars or ship-borne containers.

In accordance with yet another broad aspect, the invention provides a method for verifying the contents of a cargo container. The method comprises receiving at a first location a manifest conveying objects expected to be present in the cargo container, the manifest having been sent from a second location geographically distinct from the first location. The method also comprises acquiring at the first location an image signal associated with the cargo container, the image signal conveying information related to contents of the cargo container. The method also comprises processing the image signal associated with the cargo container in combination with the manifest and a group of target images to verify the contents of the cargo container.

Other aspects and features of the present invention will become apparent to those ordinarily skilled in the art upon review of the following description of specific embodiments of the invention in conjunction with the accompanying Figures.

BRIEF DESCRIPTION OF THE DRAWINGS

A detailed description of the embodiments of the present invention is provided herein below, by way of example only, with reference to the accompanying drawings, in which.

Figure 1:
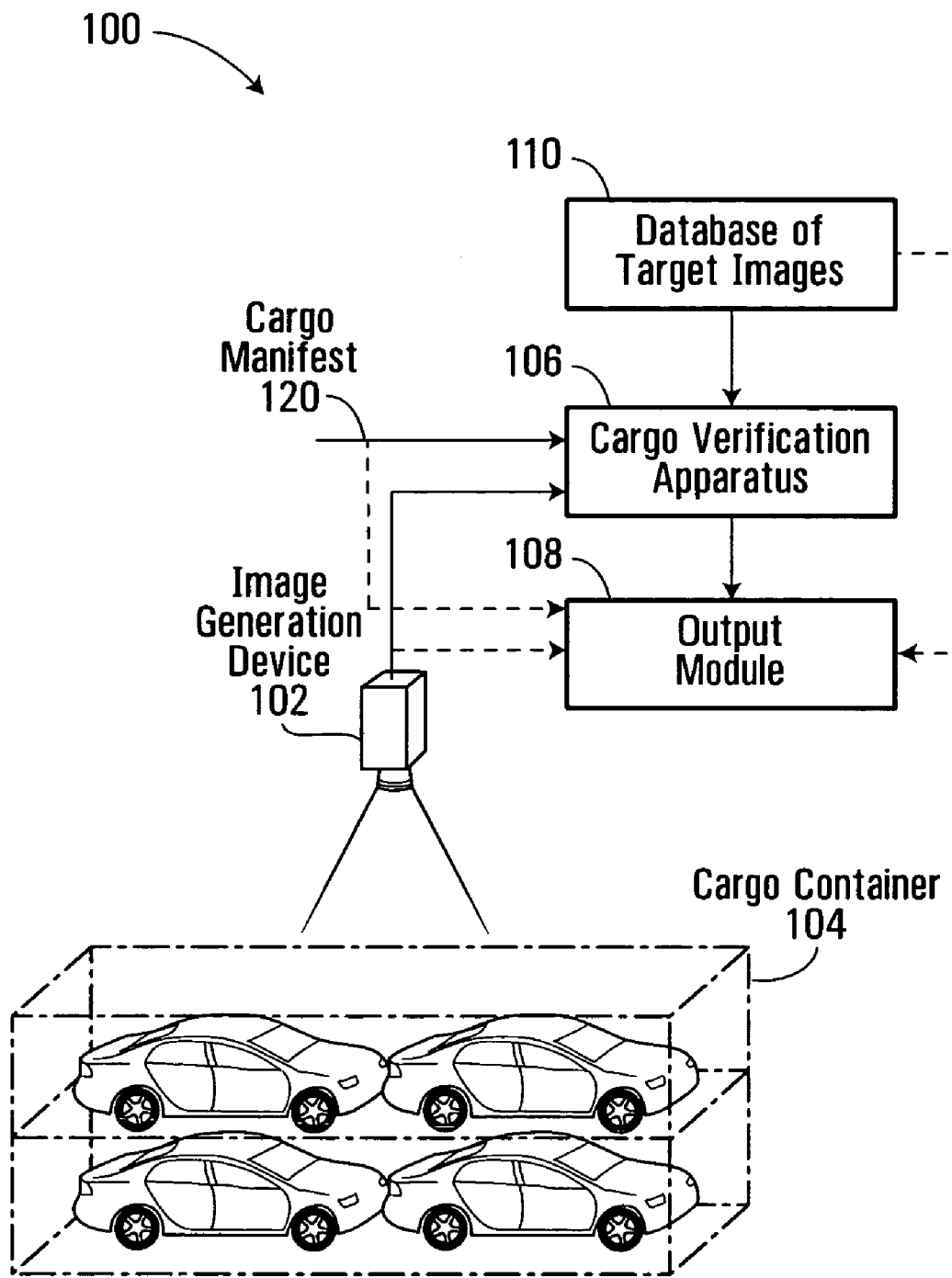
FIG. 1 is a high-level block diagram of a system for screening a cargo container in accordance with a specific example of implementation of the present invention.

In the drawings, the embodiments of the invention are illustrated by way of examples. It is to be expressly understood that the description and drawings are only for the purpose of illustration and are an aid for understanding. They are not intended to be a definition of the limits of the invention.

DETAILED DESCRIPTION

Shown in FIG. 1 is a system 100 for screening a cargo container in accordance with a specific example of implementation of the present invention. The system 100 includes an image generation device 102, an apparatus 106 in communication with the image generation device 102 and an output module 108.

The image generation device 102 generates an image signal associated with a cargo container 104. The image signal conveys information related to the contents of the cargo container 104. The apparatus 106 receives the image signal associated with the cargo container 104. The apparatus 106 also received at input 120 a list of objects conveying objects expected to be present in the cargo container.

The apparatus 106 processes the image signal associated with the cargo container in combination with the list of objects and a group of target images associated with objects to derive mismatch information data. The mismatch information data conveys distinctions, if any, between the list of objects 120 expected to be present in the cargo container 104 and information related to the contents of the cargo conveyed by the image signal generated by the image generation device 102. In a specific implementation, the group of target images is stored in a database of target images 110. Examples of the manner in which the mismatch information data can be derived are described later on in the specification. The output module 108 conveys information derived at least in part on the basis of the mismatch information data to a user of the system.

Advantageously, the system 100 provides assistance to cargo screening personnel in verifying the content of cargo containers and in identifying discrepancies between the manifest of the cargo container and the actual content of the cargo container. In addition, this verification is performed without requiring that the seal of the cargo container be broken and without requiring that an opening be made on the cargo container body.

As described above, a list of objects expected to be present in the cargo is received at input 120. The list of objects at input 120 may be provided in any suitable format capable of conveying a set of objects expected to be in cargo container 104. In the specific implementation depicted in the figure, the list of objects is derived from a cargo manifest associated with the cargo container 104. The list of objects may be in electronic format, paper format and may be in the form of text, images, a combination of text and images or in any other suitable format. In a specific practical implementation, the list of objects received is converted into a standard electronic format for ease of processing by the cargo verification apparatus 106.

In a non-limiting implementation, the input 120 may be part of a computing terminal including a user interface allowing the list of objects 120 to be entered either electronically (electronic file or otherwise) or manually (scanning, keyboard, mouse, ASR (automatic speech recognition)) and communicated to cargo verification apparatus 106. In an alternative non-limiting implementation, the input 120 is in communication with a network (LAN, WAN or other) and may receive data conveying the list of objects over that network. In yet another alternative implementation (not shown in the figures), the input 120 is in communication with a database of cargo manifests including a plurality of entries, each entry being associated to a respective cargo container. The apparatus 106 is adapted to receive an identifier data element associated to a cargo container 104 and extract a cargo manifest from the database of cargo manifests on the basis of this identifier data element. The identifier data element may be provided through in any suitable user interface including, but not limited to, optical scanners (eg. bar code), keyboard, pointing device, touch sensitive screen and voice inputs (ASR).

Image Generation Device 102

In a specific example of implementation, the image generation device 102 uses penetrating radiation or emitted radiation to generate the image associated with the cargo container 104. The radiation can be of any wavelengths and energies (e.g. any bands) of the electromagnetic spectrum. Specific examples of image generation devices that may be used include, without being limited to, x-ray, gamma ray, computed tomography (CT scans), thermal imaging and millimeter wave devices. Such devices are known in the art and as such will not be described further here. In a non-limiting example of implementation, the image generation device 102 is a conventional x-ray machine adapted for generating an x-ray image of the cargo container 104.

In a first specific example of implementation, the image generation device 102 is operative for acquiring an image conveying a single view of the cargo container. In a non-limiting example of implementation, the image generation device 102 is operative for acquiring an image of the cargo container along an axis running the length of the cargo container. This type of screening is particularly useful when the objects stored within the container are organized in a single layer in the image plane or in multiple layers on the image plane with no objects occluded by others. Examples of objects that can be screened using an image of the cargo container along a single axis include vehicles such as cars, trucks, personal watercraft devices, snowmobiles, motorcycles and other vehicles transported via containers. Other examples include any large objects with a distinct signature (e.g. shape, density, color, texture, etc.)

In a second specific example of implementation, the image generation device 102 is operative for acquiring multiple views of the cargo container. In a non-limiting example of implementation, the image generation device 102 is operative for acquiring a first view of the cargo container along a first axis running the length of the cargo container and a second view of the cargo container along a second axis running the depth of the cargo container. The combination of the first and second image allows obtaining a more complete indication of the contents of the cargo container. This type of screening is particularly useful when objects stored within the container are occluded, partially or completely, by others in the image plane.

In a third specific example of implementation, the image generation device 102 is operative for acquiring multiple views of the cargo container along a same axis axes but at different depths. Computed tomography scans (CT scans), for example, are particularly useful in such cases. In a non-limiting example of implementation, the image generation device 102 is operative for acquiring a first image of the cargo container along an axis running the length of the cargo container at a first depth and a second image of the cargo container along the same axis running the length of the cargo container at a second depth. This type of screening is particularly useful when objects stored within the container are organized in multiple layers and occluded by others in a given image plane.

In a fourth specific example of implementation, the image generation device 102 is operative for acquiring multiple views of a same surface of the cargo container but at different angles. In a non-limiting example of implementation, the image generation device 102 is operative for acquiring a first image of the cargo container along an axis running the length of the cargo container at a specific angle (say at an angle perpendicular to the surface of the cargo container) and a second image of the cargo container along the same axis but at a different angle (say at an angle of 45° to the surface of the cargo container). This type of screening is particularly useful to better pin point the location of an object in its image plane and allowing to see an object that would otherwise be hidden, while providing a 3-D effect.

In a fifth specific example of implementation, the image generation device 102 is operative for acquiring multiple images of the cargo container along a single axis but using different beam intensities. In a non-limiting example of implementation, the image generation device 102 is operative for acquiring images of the cargo container along an axis running the length of the cargo container using a z-backscatter x-ray for a first image and a high energy x-ray for a second image. The different beam intensities provide different penetration rates and thus identification of the constitution of a given object can be obtained in more details.

It will be readily appreciated by the person skilled in the art that other types of images conveying information related to the contents of cargo containers may be obtained using suitable image generation devices 102. Such types of images will become readily apparent to the person skilled in the art in light of the present description and as such will not be described further here.

Non-limiting examples of the types of image generation devices that may be used are described in the following U.S. patents:
  U.S. Pat. No. 6,292,533: Mobile X-ray inspection system for large objects, issued Sep. 18, 2001 and assigned to American Science & Engineering, Inc.
  U.S. Pat. No. 6,252,929: Mobile X-ray inspection system for large objects, issued Jun. 26, 2001 and assigned to American Science & Engineering, Inc.
  U.S. Pat. No. 5,903,623: Mobile X-ray inspection system for large objects, issued May 11, 1999, and assigned to American Science & Engineering, Inc.
  U.S. Pat. No. 5,764,683: Mobile X-ray inspection system for large objects, issued Jun. 9, 1998, and assigned to American Science & Engineering, Inc.
  U.S. Pat. No. 6,928,141: Relocatable X-ray imaging system and method for inspecting commercial vehicles and cargo containers, issued Aug. 9, 2005, and assigned to Rapiscan, Inc.

The contents of the above listed documents are incorporated herein by reference.

The image signal generated by the image generation device 102 and associated with the cargo container 104 may be conveyed as a two-dimensional (2-D) image or as a three-dimensional (3-D) image and may be in any suitable format. Possible formats include, without being limited to, VGA, SVGA, XGA, JPEG, GIF, TIFF and bitmap amongst others. Preferably, the image signal is in a format that can be displayed on a display screen.

Although the specific example of implementation of the system 100 for screening a cargo container shown in FIG. 1 depicts a single image generation device 102, alternative implementations of the systems may include multiple image generation devices without detracting from the spirit of the invention.

For the purpose of the present description and for the purpose of simplicity, a specific example of implementation of the system will be described with an image generation device 102 capable of acquiring a single image of the cargo container along an axis running the length of the cargo container. Alternative implementations with image generation devices 102 capable of acquiring multiple images of the cargo container can be implemented using the appropriate processing and data manipulation and such implementations are within the scope of the present invention.

Database of Target Images 110

In a specific example of implementation, the database of target images 110 includes a plurality of entries associated to respective target objects that the system 100 is designed to detect.

In a non-limiting implementation, for each entry associated to a target object at least one image (hereinafter referred to as a "target image") is provided in the database of target images 110. The format of the target images will depend upon the image processing algorithm implemented by the apparatus 106. More specifically, the format of the target images is such that a comparison operation can be performed by the apparatus 106 between the target images and data derived from the image signal associated with the cargo container 104.

Figure 7:
FIG. 7 shows three images associated to a object suitable for use in connection with the system depicted in FIG. 1, each image depicting the target object in a different orientation, in accordance with a specific example of implementation of the present invention.

Optionally, for each entry associated to a target object, a set of images is provided in the database of target images 110. For example, images depicting the target object in various orientations may be provided. FIG. 7 of the drawings depicts an example of arbitrary 3D orientations of a target object.

Optionally still, for each entry associated to a target object, characteristics of the target object are provided. Such characteristics may include, without being limited to, the name of the target object, its monetary value from a customs perspective, country of origin, serial number of products, etc. . . . Where the object is an illicit object, such as a weapon, illegal smuggling of people etc. . . . additional information such as the object's associated threat level, the recommended handling procedure when such a target object is detected and any other suitable information may also be provided. Optionally still, each entry in the database of target images 110 is also associated to a respective target object identifier data element.

The specific design and content of the database of target images 110 may vary from one implementation to the next without detracting from the spirit of the invention. The design of the database is not critical to the present invention and as such will not be described further here.

Although the database of target images 110 has been shown in FIG. 1 to be a component separate from the apparatus 106, it will be appreciated that in certain embodiments the database of target images 110 may be part of apparatus 106 and that such implementations do not detract from the spirit of the invention. In addition, it will also be appreciated that in certain implementations, the database of target images 110 is shared between multiple apparatuses 106.

In a yet another alternative specific implementation, the database of target images 110 is sent along with the cargo container manifest and is received as an input to the apparatus 106. In such an alternative implementation, the database of target images 110 includes a plurality of entries associated to respective target objects that are expected to be present in the cargo container 104. Optionally, in such an implementation, the database of target images 110 also includes a plurality of "imposter" target objects associated to objects not expected to be present in the cargo container 104 but whose presence it is desirable to detect. An example will better illustrate the use of imposter target objects. Let us take an example where a certain cargo container is expected to carry eight (8) VOLVO vehicle model V90. The cargo manifest includes an entry indicating that the cargo container is expected to contain eight (8) VOLVO vehicle model V90. The database of target images 110, in accordance with a non-limiting implementation would include an entry with images associated to the VOLVO vehicle model V90. As imposter objects, the database of target images may include other VOLVO vehicle models. It may also include images of other objects such as weapons, people or other objects to detect the illegal transport of such objects or people so that these objects are detected if present in the cargo container.

In a yet another specific implementation, the database of target images 110 is pre-processed in combination with the cargo container manifest received at input 120 to extract therefrom a subset of entries, the entries corresponding to objects listed in the manifest. The result of such pre-processing is a plurality of entries associated to respective target objects that are expected to be present in the cargo container 104. Advantageously, pre-processing the database of target images 110 to extract a subset therefrom allows for a reduction in the search space since fewer images of objects from the database of target images 110 need to be compared to the image associated with the cargo container. Optionally, in such an implementation, the database of target images 110 may also include "imposter" target objects.

Output Module 108

In a specific example of implementation, the output module 108 conveys to a user of the system information derived at least in part on the basis of the mismatch information data.

Figure 2:
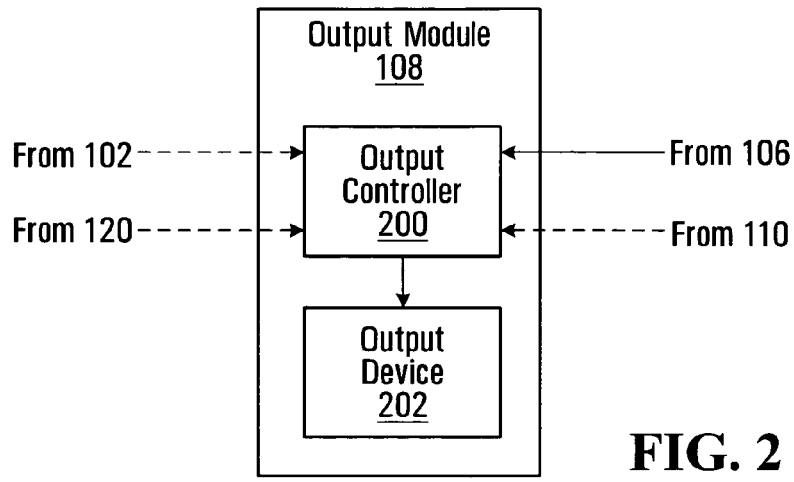
FIG. 2 is a block diagram of an output module suitable for use in connection with the system depicted in FIG. 1 in accordance with a specific example of implementation of the present invention.

A specific example of implementation of the output module 108 is shown in FIG. 2 of the drawings. As depicted, the output module includes an output device 202 and an output controller unit 200.

The output controller unit 200 receives the mismatch information data associated to the cargo container 104 from apparatus 106 (shown in FIG. 1). In a specific implementation, the mismatch information data conveys one or more objects present in the manifest or the list of object received at input 120 but absent from the objects detected in the cargo container. Alternatively, the mismatch information data convey an object detected in the container but absent from the list of objects received at input 120.

In a first specific example of implementation, the output controller unit 200 is adapted to convey mismatch information data associated to the cargo container 104. In a non-limiting example of implementation, the output controller unit 200 generates a visual representation in the form of a graphical user interface of the type depicted in FIG. 4 of the drawings. The graphical user interface 400 includes a plurality of information elements including, but not limited to:

- a container identifier element 402;
- a representation of the contents of the cargo manifest 404;
- a list of objects 406 detected in the cargo container by the screening system 100;
- mismatch information data 408; and
- additional information 414.

The container identifier data element 402 is for uniquely identifying the cargo container to which the screening process was applied. In a non-limiting implementation, the container identifier data element 402 is a user modifiable field. In such a non-limiting implementation, the container identifier data element 402 can be used to access previously stored screening results associated to a given cargo container.

The representation of the contents of the cargo manifest 404 displays a first list of objects which conveys objects expected to be present in the cargo container. In the example depicted, the first list of objects indicates that the cargo container bearing ID# 12345 is expected to contain:
- 4×VOLVO MODEL V90; and
- 1×NISSAN MODEL PATHFINDER.

The list of objects 406 detected in the cargo container by the screening system 100 is a second list of objects. In the example depicted, the second list of objects indicates that the cargo container bearing ID# 12345 was screened and as a result the following objects were detected:
- 5×VOLVO MODEL V90; and
- 10× M16—machine guns—WEAPON.

The mismatch information data 408 is displayed to the user, which conveys distinction(s), if any, between the first list of objects 404 and the second list of objects 406. The mismatch information data 408 may be displayed in any suitable fashion for conveying distinction(s) between the first list of objects 404 and the second list of objects 406. In the specific example depicted, the mismatch information data includes first data 410 conveying one or more object(s) present in the first list of objects but absent from the second list of objects. In this specific example, the first data indicates that the object: 1×NISSAN MODEL PATHFINDER is present in the first list of objects but absent from the second list of objects. In the specific example depicted, the mismatch information data also includes second data 412 conveying one or more object(s) present in second list of objects 406 (i.e. detected in the cargo container) but absent from the first list of objects 404. In this specific example, the second data 412 indicates that the objects: 1×VOLVO MODEL V90; and 10× M16—machine guns—WEAPON are present in the second list of objects but absent from the first list of objects.

Optionally, the display may further provide additional information 414 such as a recommended course of action. Other additional information such as the associated threat level of the objects detected in the container, the recommended handling procedure when such a target object is detected and any other suitable information may also be provided. In the specific example depicted in FIG. 4, the additional information 414 indicates that the mismatch information revealed that the container contained one or more restricted objects (i.e. 10× M16—machine guns—WEAPON) and that manual screening was recommended.

Figure 4:
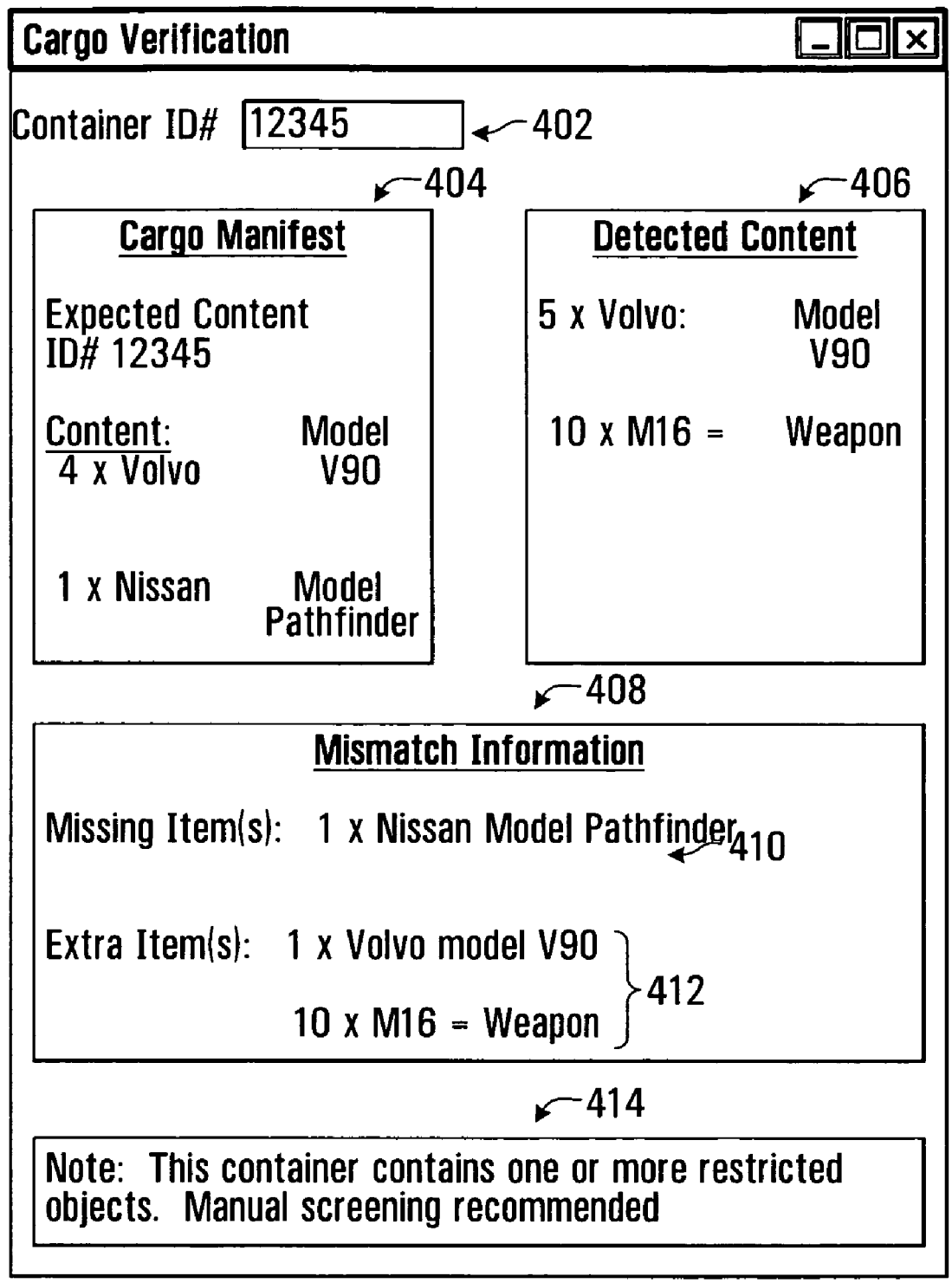
FIG. 4 depicts a specific example of a visual representation conveying mismatch information data in accordance with specific examples of implementation of the present invention.

It will be appreciated that the graphical user interface may include additional information without detracting from the spirit of the invention and that the examples illustrated in FIG. 4 have been provided for the purpose of illustration only. In addition, it will also be appreciated that certain ones of the information elements 402 404 406 408 and 414 may be omitted in certain specific implementations. In addition, although the information elements 402 404 406 408 and 414 were depicted in text format in FIG. 4, it will be readily appreciated to the person skilled in the art in light of the present description that certain ones of the information elements 402 404 406 408 and 414 may be represented as images in alternative implementations and that such alternative implementations are within the scope of the present application.

In a non-limiting example of implementation, the output controller unit 200 generates image data conveying the mismatch information in combination with the image signal associated with the cargo container 104 and generated by the image generation device 102 (shown in FIG. 1).

In a second specific example of implementation, the output controller unit 200 is adapted to cause an audio unit to convey mismatch information data associated to the cargo container 104.

The output controller unit 200 then releases a signal for causing the output device 202 to convey the desired information to a user of the system.

The output device 202 may be any device suitable for conveying mismatch information data associated to a cargo container to a user of the system 100. The information may be conveyed in visual format, audio format or as a combination of visual and audio formats. In addition, when the information is presented in visual format, it may be displayed on a video screen device, printed on a paper substrate or stored in digital format on a computer readable medium. The computer readable medium may be accessed at a later date.

In a first specific example of implementation, the output device 202 includes a display screen adapted for displaying in visual format mismatch information data associated to the cargo container 104.

In a second specific example of implementation, the output device 202 includes a printer adapted for displaying in printed format mismatch information data associated to the cargo container 104.

In a third specific example of implementation, the output device 202 includes an audio output unit adapted for releasing an audio signal conveying mismatch information data 104.

In a fourth specific example of implementation, the output device 202 includes a set of visual elements, such as lights or other suitable visual elements, adapted for conveying in visual format mismatch information data associated to the cargo container 104. For example, a green light may indicate that the objects expected to be in the cargo container 104 have all been successfully detected and no additional objets have been detected. Yellow and red lights may indicate that there are certain discrepancies between the objects expected to be in the cargo container 104 and the objects detected or that an unexpected "restricted" object has been detected.

The person skilled in the art will readily appreciate, in light of the present specification, that other suitable types of output devices may be used here without detracting from the spirit of the invention.

Apparatus 106

Figure 3:
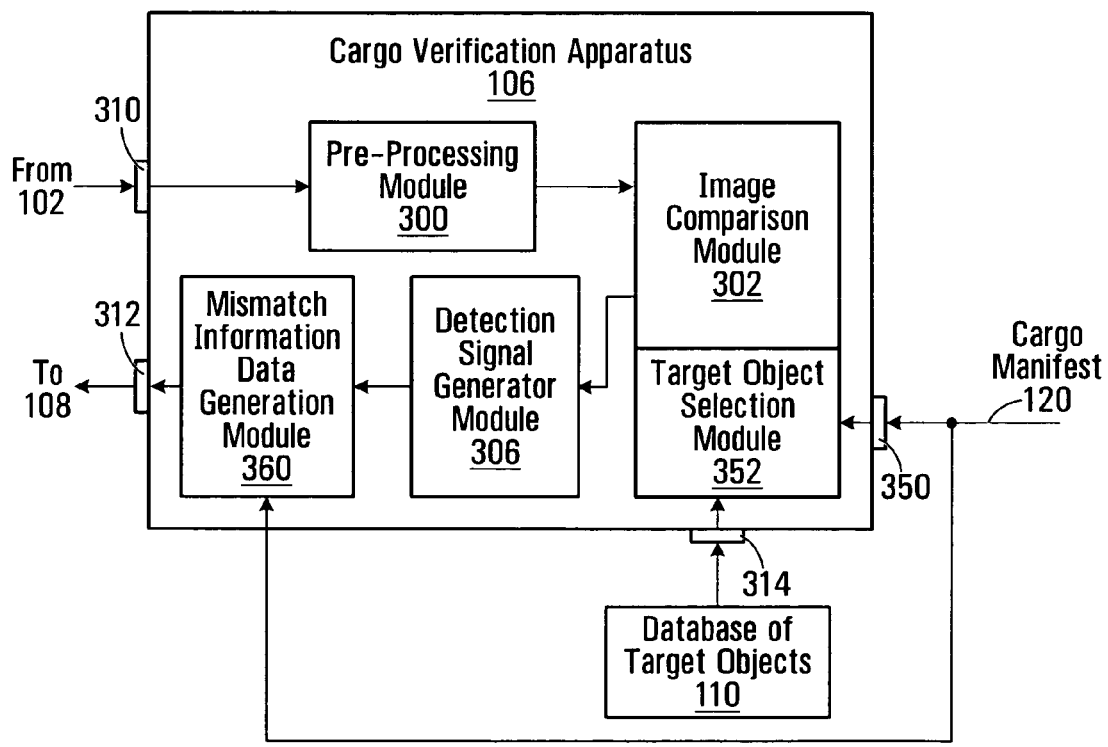
FIG. 3 is a block diagram of an apparatus for processing images suitable for use in connection with the system depicted in FIG. 1 in accordance with a specific example of implementation of the present invention.

The cargo verification apparatus 106 will now be described in greater detail with reference to FIG. 3. As depicted, the apparatus 106 includes a first input 310, a second input 350, a third input 314, an output 312 and a processing unit, generally comprising a pre-processing module 300, an image comparison module 302, a target object selection module 352, a detection signal generator module 306 and a mismatch information data generation module 360.

The first input 310 is for receiving an image signal associated with a cargo container from the image generation device 102 (shown in FIG. 1).

The second input 350 is in communication with system input 120 and is for receiving information conveying the expected content of the cargo container. In a specific implementation, the information conveying the expected content of the cargo container is derived from the manifest associated to the cargo container.

The third input 314 is for receiving target images from the database of target images 110. It will be appreciated that in embodiments where the database of target images 110 is part of apparatus 106, the third input 314 may be omitted.

The output 312 is for releasing mismatch information data associated with the cargo container 104 for transmittal to output module 108.

Figure 5:
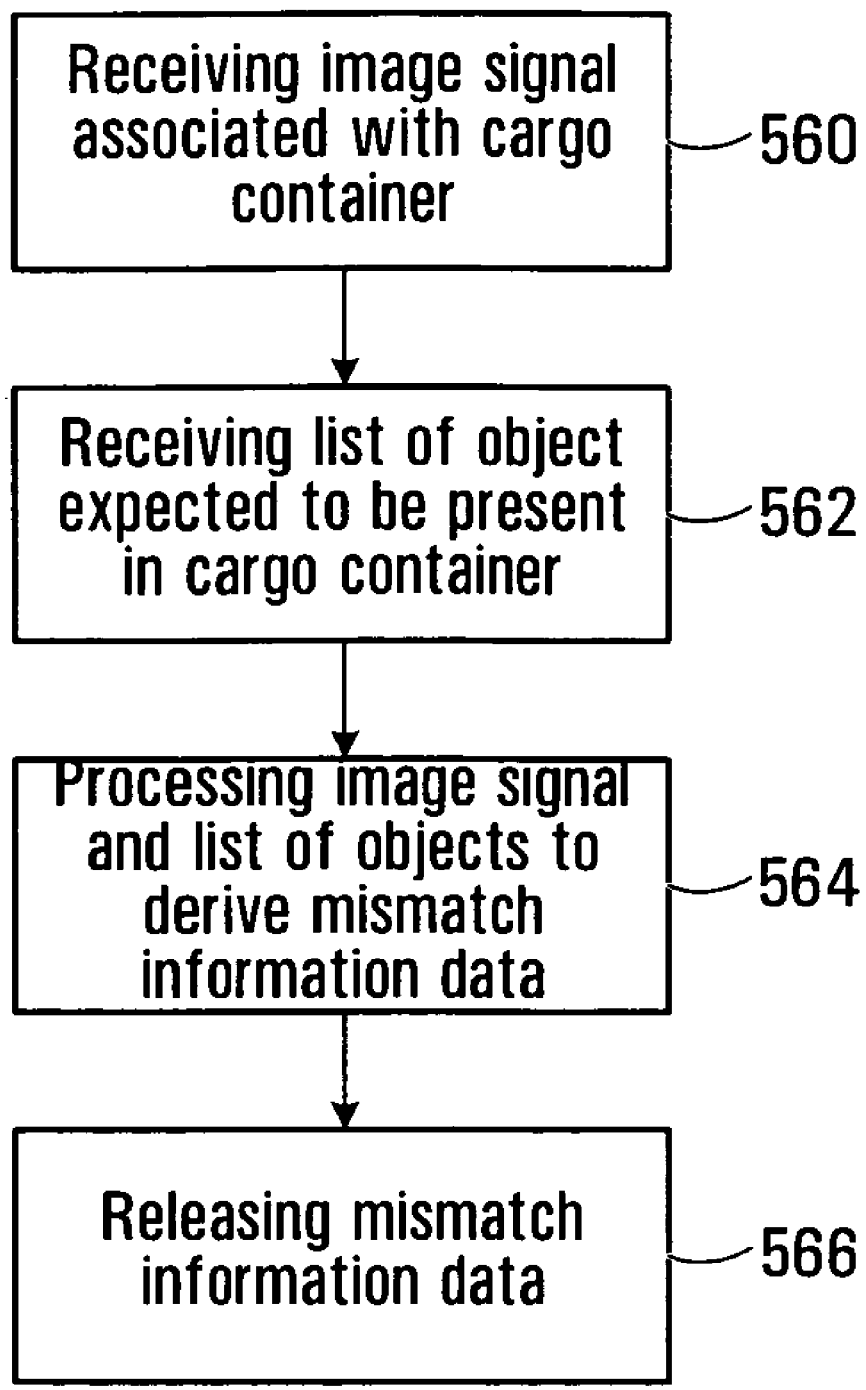
FIG. 5 is a flow diagram depicting a process for screening a cargo container in accordance with a specific example of implementation of the present invention.

The process implemented by the processing unit of the apparatus 106 is depicted in FIG. 5 of the drawings. At step 560, the processing unit of the apparatus 106 receives from the first input 310 the image signal associated with the cargo container 104. At step 562, the processing unit of the apparatus 106 receives from input 350 a list of objects expected to be present in the cargo container 104. At step 564, the processing unit processes the image signal associated with the cargo container 104 and the information received at second input 350 in combination with a plurality of target images associated with target objects received at third input 314 to derive mismatch information data. The mismatch information data conveys at least one distinction between the list of objects received at second input 350 and the information related to the contents of the cargo container conveyed by the image signal received at the first input 310. At step 566, the processing unit of the apparatus 106 generates and releases at output 312 information conveying the mismatch information data.

Figure 6:
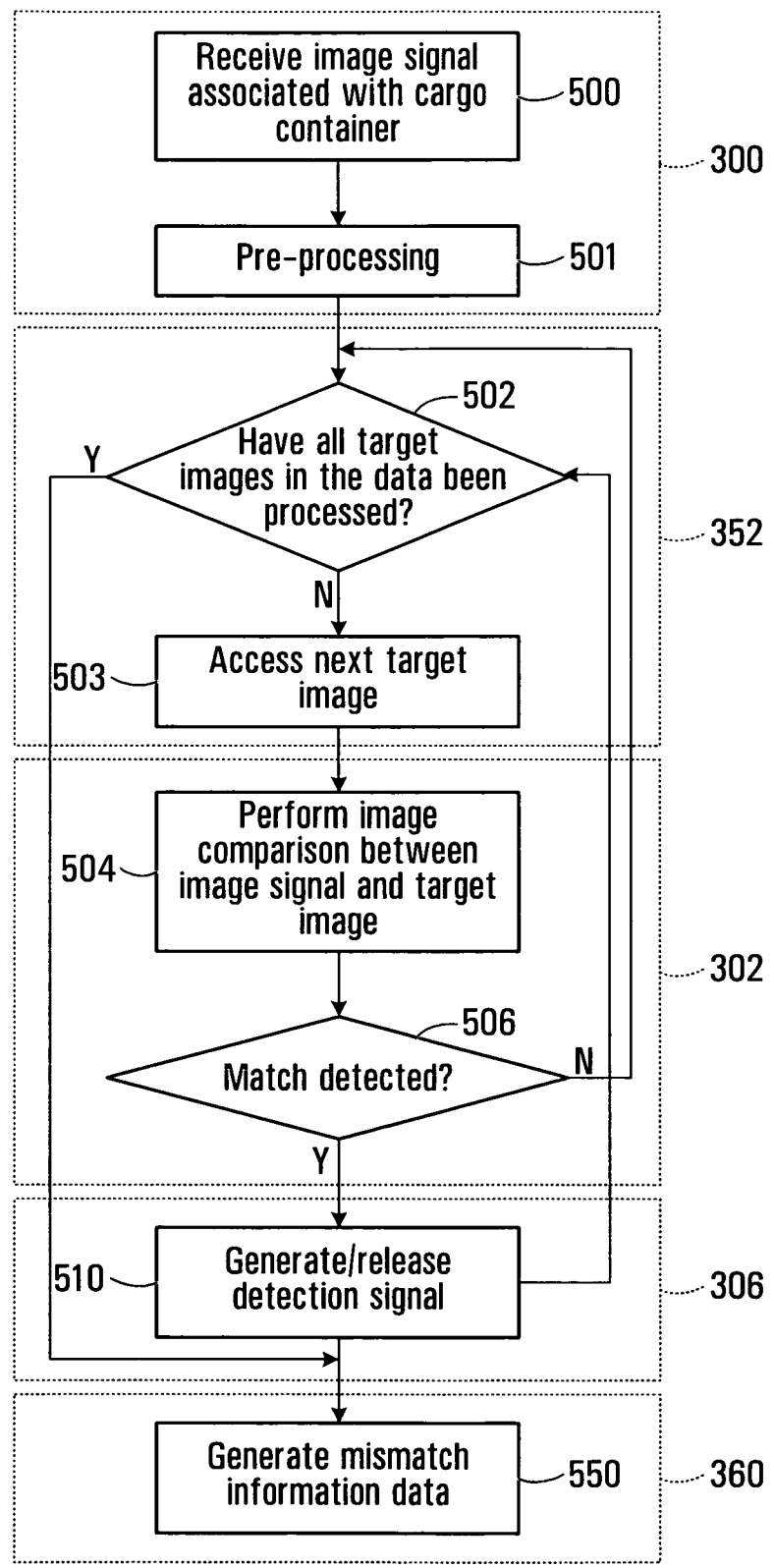
FIG. 6 is a flow diagram depicting a process for deriving mismatch information data for a cargo container in accordance with a specific example of implementation of the present invention.

The process implemented by the various functional elements of the processing unit of the apparatus 106 will now be described with reference to FIG. 6 of the drawings. At step 500, the pre-processing module 300 receives an image signal associated with the cargo container 104 via the first input 310. At step 501, the pre-processing module 300 processes the image signal in order to enhance the image, remove extraneous information therefrom and remove noise artefacts in order to obtain more accurate comparison results. The complexity of the requisite level of pre-processing and the related tradeoffs between speed and accuracy depend on the application. Examples of pre-processing may include, without being limited to, brightness and contrast manipulation, histogram modification, noise removal and filtering amongst others. It will be appreciated that all or part of the functionality of the pre-processing module 300 may actually be external to the apparatus 106, e.g., it may be integrated as part of the image generation device 102 or as an external component. It will also be appreciated that the pre-processing module 300 (and hence step 501) may be omitted in certain embodiments of the present invention without detracting from the spirit of the invention. As part of step 501, the pre-processing module 300 releases a modified image signal for processing by the image comparison module 302.

At step 502, the target object selection module 352 verifies whether there remains any unprocessed target images in the database of target images 110. In the affirmative, the image comparison module 302 proceeds to step 503 where the next target image is accessed and the process then proceeds to step 504. If at step 502 all target images in the database of target images 110 have been processed, the process moves on to step 550 sending a signal to the mismatch information data generation module that all the target objects have been processed.

Optionally (not shown in the figures), prior to step 502, the target object selection module 352 is adapted for processing the database of target images 110 on the basis of the list of objects expected to be in the cargo container and received at input 120 to derive a group of target images. The group of target images is a subset of the database of target images and includes entries associated to objects expected to be present in the cargo container 104 (FIG. 1). Optionally, the subset of the database of target images is augmented with a set of entries associated to imposter objects, the impostor objects being indicative of objects which are not expected to be in the cargo container 104 but whose presence it is desirable to detect. Non-limiting examples of impostor objects include contraband weapons, human cargo or any other objects that are desirable to detect. In such optional implementations, the process steps 502 503 504 506 are performed on the subset of the database of target images instead of on the entire database 110.

At step 504, the image comparison module 302 compares the image signal associated with the cargo container 104 against the target image accessed at step 503 to determine whether a match exists. The comparison may be effected using any image processing algorithm suitable for comparing two images. Examples of algorithms that can be used to perform image processing and comparison include without being limited to:

A—Image Enhancement
  Brightness and contrast manipulation
  Histogram modification
  Noise removal
  Filtering B—Image Segmentation
  Thresholding
    Binary or multilevel
    Hysteresis based
    Statistics/histogram analysis
  Clustering
  Region growing
  Splitting and merging
  Texture analysis
  Watershed
  Blob labeling C—General Detection
  Template matching
  Matched filtering
  Image registration
  Image correlation
  Hough transform D—Edge Detection
  Gradient
  Laplacian E—Morphological Image Processing
  Binary
  Grayscale F—Frequency Analysis
  Fourier Transform
  Wavelets G—Shape Analysis and Representations
  Geometric attributes (e.g. perimeter, area, euler number, compactness)
  Spatial moments (invariance)
  Fourier descriptors
  B-splines
  Chain codes
  Polygons
  Quad tree decomposition H—Feature Representation and Classification
  Bayesian classifier
  Principal component analysis
  Binary tree
  Graphs
  Neural networks
  Genetic algorithms
  Markov random fields The above algorithms are well known in the field of image processing and as such will not be described further here.

In a specific example of implementation, the image comparison module 302 includes an edge detector to perform part of the comparison at step 504. In another specific example of implementation, the comparison performed at step 504 includes effecting a correlation operation between data derived from the image signal and the target images selected at step 503. In a specific example of implementation, the correlation operation is performed by an optical correlator. A specific example of implementation of an optical correlator suitable for use in comparing two images will be described later on in the specification. In an alternative example of implementation, the correlation operation is performed by a digital correlator.

The image comparison module 302 then proceeds to step 506 where the result of the comparison effected at step 504 is processed to determine whether a match exists between the image signal associated with the cargo container 104 and the target image. In the absence of a match, the image comparison module 302 returns to step 502. In response to detection of a match, the image comparison module 302 triggers the detection signal generation module 306 to execute step 510. Then, the process then returns to step 502 to continue processing with respect to the next target image.

At step 510, the detection signal generation module 306 generates a detection signal conveying the presence of the target object in the cargo container 104, and the detection signal is transmitted to the mismatch information data generation module 360, which implements step 550.

At step 550, the mismatch information data generation module 360 processes the detection signal(s) received from the detection signal generation module 306 and conveying the presence of the target object in the cargo container 104 in combination with the list of objects received at input 350 conveying the objects expected to be present in the cargo container to generate mismatch information data. In a specific example of implementation, the list of objects received at input 350 is a first list of objects and the mismatch information data generation module 360 is adapted to generate a second list of objects on the basis of the detection signal(s) received from the detection signal generation module 306. The second list of objects conveys objects whose presence in the cargo container 104 was detected by the image comparison module 302. The mismatch information data generation module 360 is operative to compare the second list of objects with the first list of objects to derive the mismatch information data. The mismatch information data conveys object(s) present in the first list of objects but absent from the second list of objects or, alternatively object(s) present in the second list of objects but absent from the first list of objects. Optionally, at step 550 additional information associated to the mismatch information data may also be generated. In a specific example of implementation, for an object present in the second list of objects but absent from the first list of objects (i.e. an object not expected to be in the cargo container but which was detected), such additional information may include the object's associated threat level, the recommended handling procedure when such a target object is detected and any other suitable information. Such additional information may be stored in the database of target objects 110 in association with each object (or category of objects) or may be derived separately on the basis of heuristic rules and recognized best practice rules.

Optionally, at step 550, the mismatch information data generation module 360 is adapted for generating log information data elements conveying the mismatch information data (and optionally additional information of the type described above). In addition to this information, such log information data elements could also include the type of object(s) detected, the location of the detection, the time of the detection, an identification of the screening personnel present at the time the detection was performed, an identification of the machine which performed the detection, the flight/ship or other vehicle involved, cargo owner information, the image of the cargo container generated by the image generation device 102 and any other suitable type of information. This information can be used to track performance, to gather statistical information and perform trend analysis. It can also be used to ensure that screening personnel is both efficient and diligent in screening. The log information is then stored on a computer readable storage medium and/or sent over a network to a pre-determined location for viewing or further processing.

The mismatch information data, and optionally the additional information associated to the mismatch information data, are released at output 312. The mismatch information data may simply convey the fact that there is a difference between the expected content of the cargo container and the detected content, without necessarily specifying the identity of the objects missing from the cargo container or detected in the cargo container but not present in the list of expected objects. Alternatively, the mismatch information data may convey the actual identity of the objects missing from the cargo container or detected in the cargo container but not present in the list of expected objects.

Specific Example of Image Comparison Module 302 Including an Optical Correlator As mentioned above, in a specific implementation of the image comparison module 302, step 504, which involves a comparison between the image signal associated with the cargo container 104 and the target images from the database of target images 110, is performed using a correlation operation. The correlation operation multiplies together the Fourier transform of the image signal associated with the cargo container 104 with the Fourier transform complex conjugate of a target image. The result of the correlation operation provides a measure of the degree of similarity between the two images.

In a specific implementation, the image comparison module 302 includes an optical correlator unit for computing the correlation between the image signal associated with the cargo container 104 and a target image from the database of target images 110. Specific examples of implementation of the optical correlator include a joint transform correlator (JTC) and a focal plane correlator (FPC).

The optical correlator multiplies together the Fourier transform of the image signal associated with the cargo container 104 with the Fourier transform complex conjugate of a target image and records the result with a camera. An energy peak measured with that camera indicates a match between the image signal associated with the cargo container 104 and the target image.

Advantageously, an optical correlator performs the correlation operation physically through light-based computation, rather than by using software running on a silicon-based computer, which allows computations to be performed at a higher speed than is possible with a software implementation and thus provides for improved real-time performance.

It will be appreciated that the correlation computation may also be implemented using a digital correlator. The correlation operation is computationally intensive and, in certain implementations requiring real-time performance, the use of a digital correlator may not provide suitable performance. In such implementations, an optical correlator will be preferred.

As described above, the correlation computation is performed between an images associated with the cargo container 104 and the target images from the database of target images 110, which includes a plurality of target images associated to objects, which the system 100 is designed to detect. It will be appreciated that the content and format of the database of target images 110 may vary from one implementation to the next. The next paragraphs describe manners in which the database 110 can be generated when a correlation computation is used to effect a comparison between an images associated with the cargo container 104 and the target images from the database of target images 110. The skilled person in the art will readily appreciate in light of the present description that other manners for generating the database 110 may be used without detracting from the spirit of the invention.

In a specific example of implementation, the database of target images 110 includes data indicative of the Fourier transform of the target image. This data will herein be referred to as a template or filter. In non-limiting examples of implementation, the Fourier transform of the target image is digitally pre-computed such as to improve the speed of the correlation operation when the system is in use. Image processing and enhancement can be performed on an original image of a target object to obtain better matching performance depending on the environment and application.

In a non-limiting example of implementation, the generation of the reference template or filter is performed in a few steps. First, the background is removed from the target image. In other words the target image is extracted from the background and the background is replaced by a black background. The resulting image is then processed through a Fourier transform function. The result of this transform is a complex image. A phase only filter (POF) for example will only contain the complex conjugate of the phase information (between zero and 2 pi) which is mapped to a 0 to 255 range values. These 256 values correspond in fact to the 256 levels of gray of an image. The person skilled in the art, in light of the present specification, will readily appreciate that various types of templates or filters can be generated. Many methods for generating Fourier filters are known in the art and a few such methods will be described later on in the specification. The reader is invited to refer to the following document for additional information regarding phase only filters (POF): "*Phase-Only Matched Filtering*", Joseph L. Horner and Peter D. Gianino, Appl. Opt. Vol. 23 no. 6, 15 Mar. 1994, pp. 812-816. The contents of this document are incorporated herein by reference.

As a variant, in order to reduce the amount of data needed to represent the whole range of 3D orientations that a single target object can take, a MACE (Minimum Average Correlation Energy) filter is used to generate a template or filter for a given target object. Typically, the MACE filter combines several different 2D projections of a given object and encodes them in a single MACE filter instead of having one 2D projection per filter. One of the benefits of using MACE filters is that the resulting database of target images 110 would take less space since it would include fewer items. Also, since the number of correlation operations needed to identify a single target object would be reduced, the total processing time to determine whether a given object is present would also be reduced. The reader is invited to refer to the following document for additional information regarding MACE filters: Mahalanobis, A., B. V. K. Vijaya Kumar, and D. Casasent (1987); Minimum average correlation energy filters, Appl. Opt. 26 no. 17, 3633-3640. The contents of this document are incorporated herein by reference.

Figure 8:
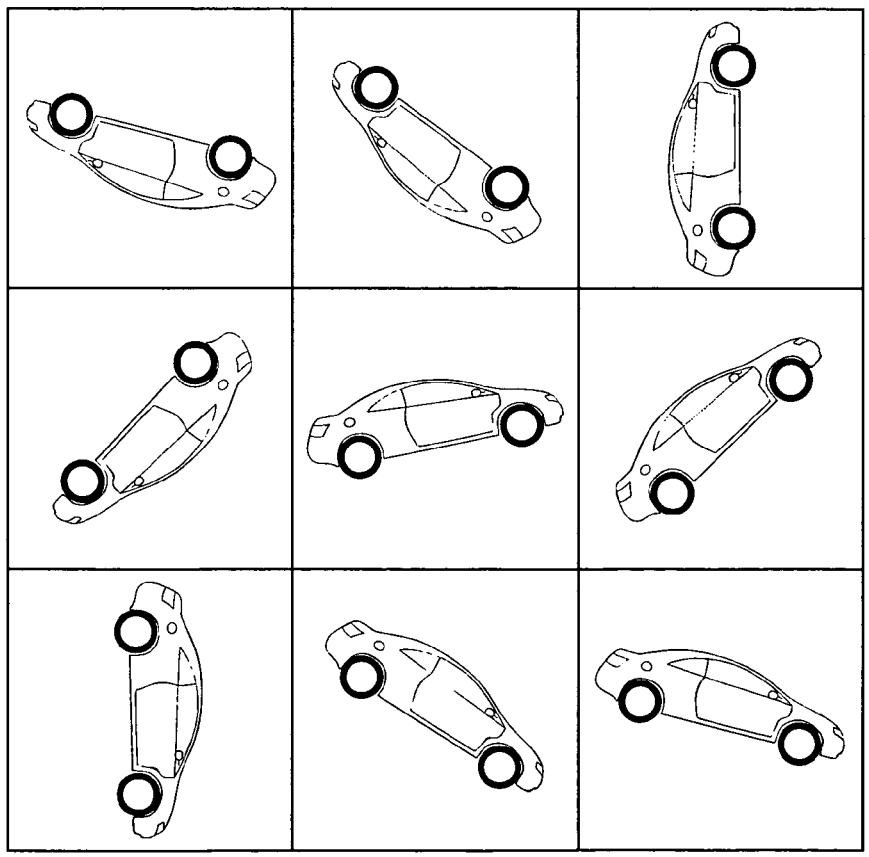
FIG. 8 shows a mosaic image including a plurality of sub-images associated with an object suitable for use in connection with the system depicted in FIG. 1, each sub-image depicting the target object in a different orientation and scale, in accordance with a specific example of implementation of the present invention.

Another way of reducing the processing time of the correlation computation is to take advantage of the linear properties of the Fourier transform. By dividing the target image into several sub-images, a composite image can be formed, herein referred to as a mosaic. When a mosaic is displayed at the input of the correlator, the correlation is computed simultaneously on all the sub-images without incurring any substantial time penalty. A mosaic may contain several different target objects or several different orientations of the same target object or a combination of both. FIG. 8 of the drawings depicts a mosaic including a target object in various orientations and scales. The parallel processing capabilities of a mosaic effectively increase the throughput of an optical correlator. The reader is invited to refer to the following document for additional information regarding the use of a mosaic in an optical correlator: Method and apparatus for evaluating a scale factor and a rotation angle in image processing, Alain Bergeron et al., U.S. Pat. No. 6,549,683, Apr. 15, 2003. The contents of this document are incorporated herein by reference.

Figure 9:
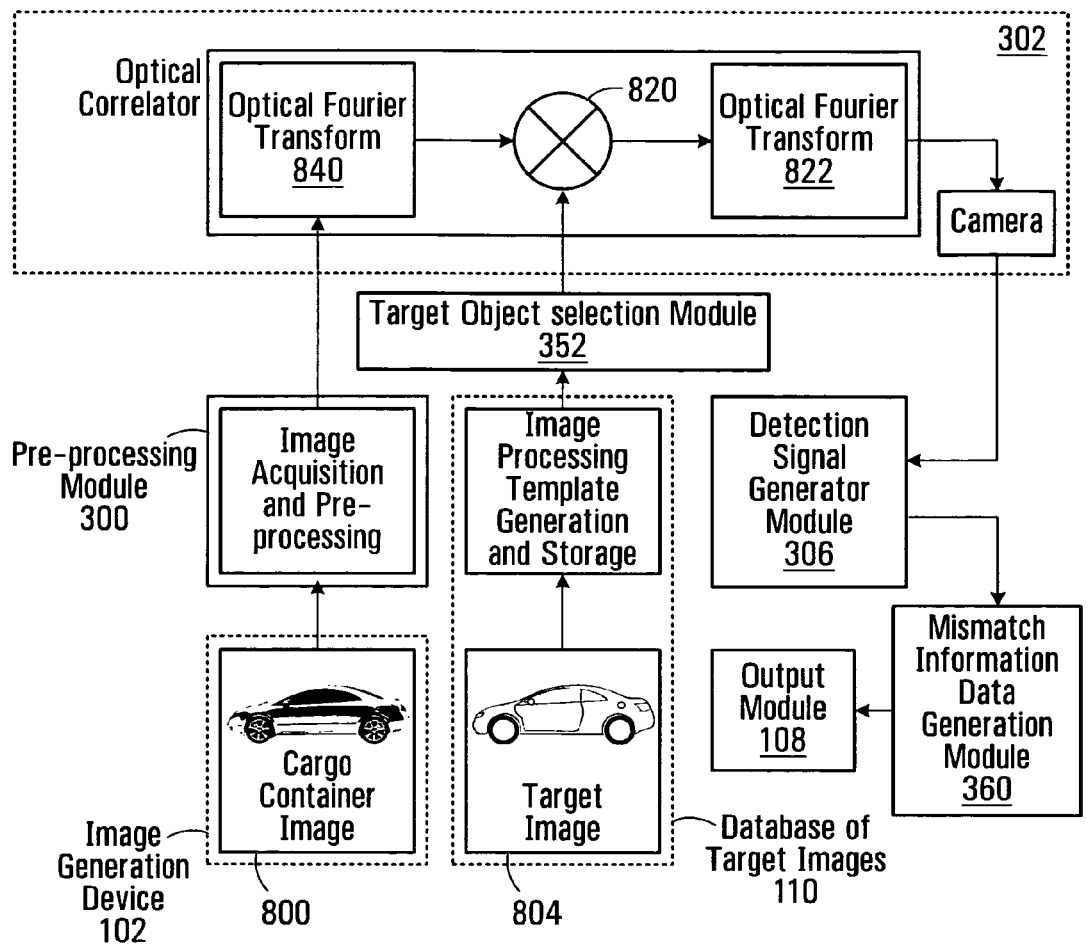
FIG. 9 is a functional block diagram a cargo container screening system including an optical correlator in accordance with a specific example of implementation of the present invention.
Figure 9:
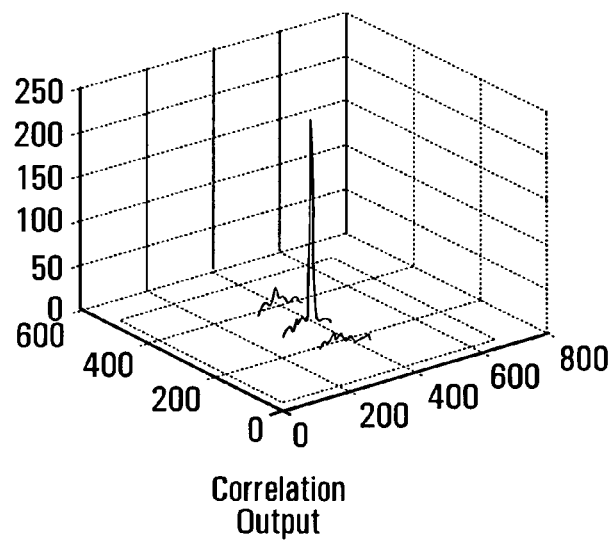

FIG. 9 depicts a high level functional block diagram a cargo container screening system using an optical correlator as part of the image comparison module 302. As shown, an image 800 associated with a cargo container is generated by the image generation device 102 and provided as input to the pre-processing module 300. The pre-processing module 300 performs pre-processing operations and forwards the pre-processed signal to the optical correlator, which is part of the image comparison module 302. At the optical correlator, the pre-processed image undergoes an optical Fourier transformation 840. The result of the transformation is multiplied 820 by the (previously computed) Fourier transform complex conjugate of a target image 804 obtained from the database of target images 110. The optical correlator then processes the result of the multiplication of the two Fourier transforms by applying another optical Fourier transform 822. The resulting signal is captured by a camera at what is referred to as the correlation plane, which yields the correlation output. The correlation output is released for transmission to the detection signal generator 306 where it is analyzed. A peak in the correlation output indicates a match between the image 800 associated with the cargo container 104 and the target image 804. The result of the detection signal generator 306 is then conveyed to the mismatch information generation module 360 which processes the detection signals to generate mismatch information data. The result of the processing is then conveyed to the user by output module 108.

In a non-limiting example of implementation of an optical correlator, the Fourier transform of the image 800 associated with the cargo container 104 is performed as follows: The image is displayed internally on a small Liquid Crystal Display (LCD). A collimated coherent light beam projects the image through a lens that performs the equivalent of a Fourier transform on the image. The multiplication 820 of the Fourier transform of the image 800 by the (previously computed) Fourier transform complex conjugate of a target image 804 is performed by projecting the Fourier transform of the image 800 on a second LCD screen on which is displayed the template or filter associated to the target image 804. The two multiplied Fourier transforms are then processed through a second Fourier lens, which forces the light beam image to a CCD (camera) at the correlation plane. The CCD output is then sent to the detection signal generator module 306. In a specific implementation, the detection signal generator module 306 includes a frame grabber implemented by a digital computer. The digital computer is programmed to detect correlation peaks captured by the CCD.

Figure 10:
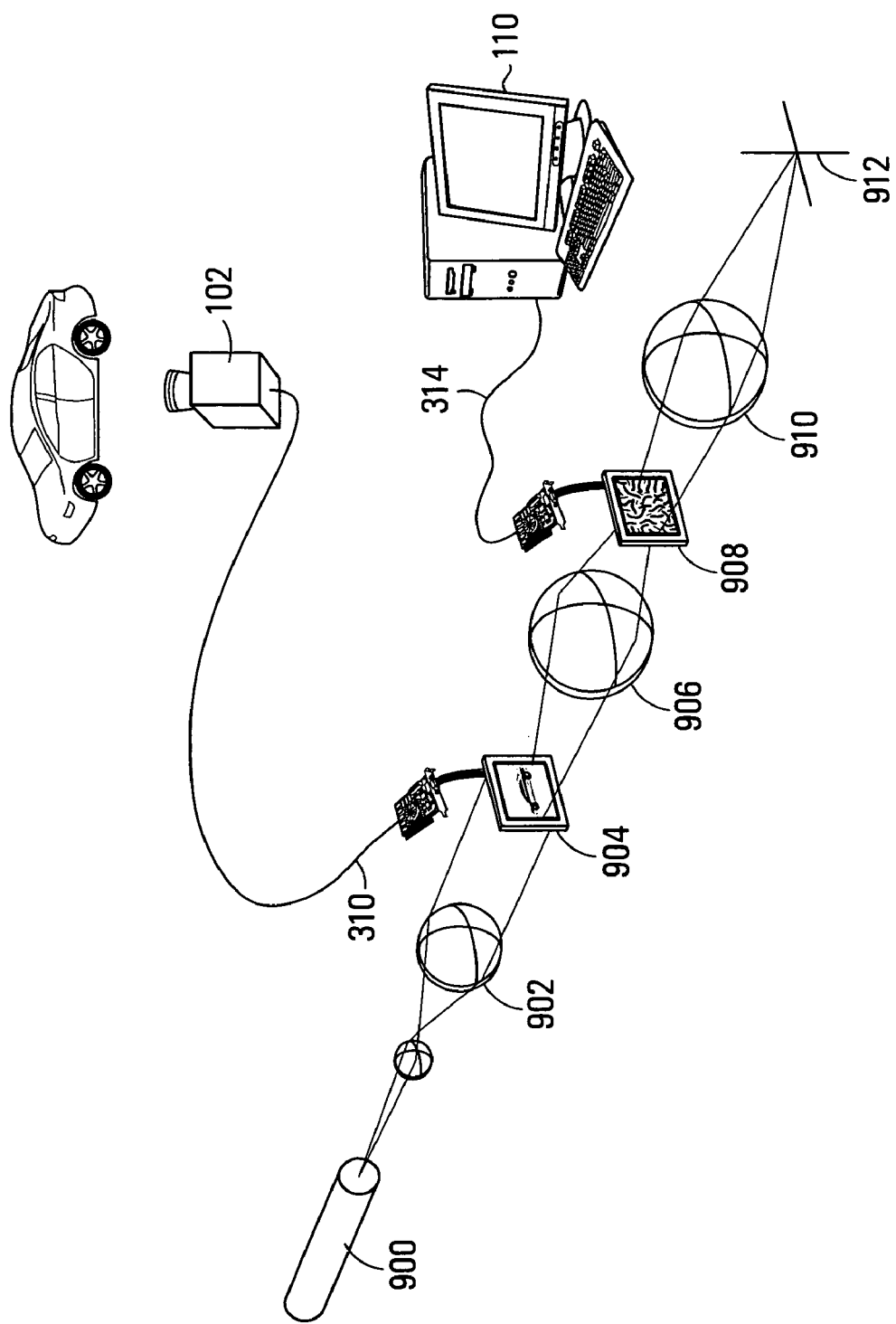
FIG. 10 is a block diagram depicting the functioning of an optical correlator in accordance with a specific example of implementation of the present invention.

The inner workings of the aforementioned non-limiting example optical correlator are illustrated in FIG. 10. On the left hand side appears a laser source 900 that generates a coherent light beam used to project images across the correlator. The light beam is directed first through a small set of lenses 902 used to expand its diameter in order to illuminate, in parallel, the whole surface of a first LCD screen 904. The image 800 associated with the cargo container 104 is displayed on the first LCD screen 904 either through a direct camera interface or provided as a VGA image by a computing device. The first LCD screen 904 is illuminated by the light beam and the image is propagated through the correlator. In the illustrated example, the image 800 captured by the camera is that of a car on a conveyor belt.

The light beam modulated by the first image on the first LCD screen 904 is then propagated through a second set of lenses 906, referred to as a Fourier lens since it performs the equivalent of the Fourier transform mathematical operation. The inherent properties of light are used to physically perform the appropriate calculations. Specifically, the propagation of light is a function which corresponds to the kernel of the Fourier transform operation, thus the propagation of light along the axis of a Fourier lens represents a sufficiently strong approximation of this natural phenomenon to assert that the light beam undergoes a Fourier transform. Otherwise stated, a lens has the inherent property of performing a Fourier transform on images observed at its front focal plane, provided that this image is displayed at its back focal plane. The Fourier transform, which can normally be rather computation-intensive when calculated by a digital computer, is performed in the optical correlator simply by the propagation of the light. The mathematics behind this optical realization is equivalent to the exact Fourier transform function and can be modeled with standard fast Fourier algorithms. For more information regarding Fourier transforms, the reader is invited to consider B. V. K. Vijaya Kumar, Marios Savvides, Krithika Venkataramani, and Chunyan Xie, "Spatial frequency domain image processing for biometric recognition", Biometrics ICIP Conference 2002 or alternatively J. W. Goodman, Introduction to Fourier Optics, 2nd Edition, McGraw-Hill, 1996. The contents of these documents are incorporated herein by reference.

After going through the Fourier lens 906, the signal is projected on a second LCD screen 908 on which is displayed the target template, i.e., Fourier transform of the target image. When the Fourier transform of the image associated with the cargo container goes through the second LCD screen 908 on which the target template is displayed, the light beam crosses a second Fourier lens 910 which, again, optically computes the equivalent of a Fourier transform multiplication. This operation corresponds to a correlation in the spatial domain. The target image displayed on the second LCD screen 908 in fact induces a phase variation on the incoming light beam. Each pixel can potentially induce a phase change whose magnitude is equivalent to its grey level. As such the Fourier transform displayed on the first LCD screen 904 is multiplied with the Fourier transform of the target image, which is equivalent to performing a correlation.

The second Fourier lens 910 finally concentrates the light beam on a small area camera or CCD 912 where the result of the correlation is measured, so to speak. The CCD (camera) 912 in fact measures energy peaks on the correlation plane. The position of a correlation peak corresponds in fact to the location of the target object center in the image 800 associated with the cargo container.

Referring back to FIG. 9, the CCD (or camera) communicates the signal from the optical correlator to the detection signal generator module 306. In this specific implementation, the detection signal generator module 306 is a computing unit including a frame grabber and software. The software is adapted to processing the signal received from the correlator to detect energy peaks as gray level video signals varying between 0 and 255. A strong intensity peak on the correlation plane indicates a match between the image 800 associated with the cargo container and the target image 804. The location of the energy peak also indicates the location of the center of the target image in the image 800 associated with the cargo container.

Fourier Transform and Spatial Frequencies

The Fourier transform as applied to images will now be described in general terms. The Fourier transform is a mathematical tool used to convert the information present within an object's image into its frequency representation. In short, an image can be seen as a superposition of various spatial frequencies and the Fourier transform is a mathematical operation used to compute the intensity of each of these frequencies within the original image. The spatial frequencies represent the rate of variation of image intensity in space. Consequently, a smooth or uniform pattern mainly contains low frequencies. Sharply contoured patterns, by contrast, exhibit a higher frequency content.

The Fourier transform of an image f(x,y) is given by:

$$F(u,v) = \iint f(x,y) e^{-j2\pi(ux+vy)} dx dy \quad (1)$$

where u, v are the coordinates in the frequency domain. Thus, the Fourier transform is a global operator: changing a single frequency of the Fourier transform affects the whole object in the spatial domain.

A correlation operation can be mathematically described by:

$$C(\varepsilon, \xi) = \int_{-\infty}^{\infty} \int_{-\infty}^{\infty} f(x,y) h^*(x-\varepsilon, y-\xi) dx dy \quad (2)$$

where $\varepsilon$ and $\xi$ represent the pixel coordinates in the correlation plane, $C(\varepsilon,\xi)$ stands for the correlation, x and y identify the pixel coordinates of the input image, f(x, y) is the original input image and $h^*(\varepsilon,\xi)$ is the complex conjugate of the correlation filter.

In the frequency domain the same expression takes a slightly different form:

$$C(\varepsilon,\xi) = \Im^{-1}(F(u,v)H^*(u,v)) \quad (3)$$

where $\Im$, is the Fourier transform operator, u and v are the pixel coordinates in the Fourier plane, F(u,v) is the Fourier transform complex conjugate of F(u,v) acquired with the camera f(x,y) and H*(u,v) is the Fourier transform of the filter of the reference template.

Thus, the correlation between an input image and a target template is equivalent, in mathematical terms, to the multiplication of their respective Fourier transform, provided that the complex conjugate of the filter is used. Consequently, the correlation can be defined in the spatial domain as the search for a given pattern (template), or in the frequency domain, as filtering operation with a specially designed matched filter.

Advantageously, the use of optics for computing a correlation operation allows the computation to be performed in a shorter time than by using a digital implementation of the correlation. It turns out that an optical lens properly positioned (i.e. input and output images are located on the lens's focal planes) automatically computes the Fourier transform of the input image. In order to speed up the computation of the correlation, the Fourier transform of a target image can be computed beforehand and submitted to the correlator as a mask or template. The target template (or filter in short) is generated by computing the Fourier transform of the reference template. This type of filter is called a matched filter.

Figure 11:
FIG. 11 depicts a Fourier transform, amplitude and phase, of the spatial domain image for number 2.

FIG. 11 depicts the Fourier transform of the spatial domain image of a '2'. It can be seen that most of the energy (bright areas) is contained in the central portion of the Fourier transform image which correspond to low spatial frequencies (the images are centred on the origin of the Fourier plane). The energy is somewhat more dispersed in the medium frequencies and is concentrated in orientations representative of the shape of the input image. Finally, little energy is contained in the upper frequencies. The right-hand-side image shows the phase content of the Fourier transform. The phase is coded from black (0°) to white (360°).

Generation of Filters from Target Images

Matched filters, as their name implies, are specifically adapted to respond to one image in particular: they are optimized to respond to an object with respect to its energy content. Generally, the contour of an object corresponds to its high frequency content. This can be easily understood as the contour represent areas where the intensity varies rapidly (hence a high frequency).

In order to emphasize the contour of an object, the matched filter can be divided by its module (the image is normalized), over the whole Fourier transform image. The resulting filter is called a Phase-Only Filter (POF) and is defined by:

$$POF(u,v) = \frac{H*(u,v)}{|H*(u,v)|} \quad (4)$$

The reader is invited to refer to the following document for additional information regarding phase only filters (POF): "*Phase-Only Matched Filtering*", Joseph L. Homer and Peter D. Gianino, Appl. Opt. Vol. 23 no. 6, 15 Mar. 1994, pp. 812-816. The contents of this document are incorporated herein by reference.

Because these filters are defined in the frequency domain, normalizing over the whole spectrum of frequencies implies that each of the frequency components is considered with the same weight. In the spatial domain (e.g. usual real-world domain), this means that the emphasis is given to the contours (or edges) of the object. As such, the POF filter provides a higher degree of discrimination, sharper correlation peaks and higher energy efficiency.

The discrimination provided by the POF filter, however, has some disadvantages. It turns out that, although the optical correlator is somewhat insensitive to the size of the objects to be recognized, the images are expected to be properly sized, otherwise the features might not be registered properly. To understand this requirement, imagine a filter defined out of a given instance of a '2'. If that filter is applied to a second instance of a '2' whose contour is slightly different, the correlation peak will be significantly reduced as a result of the great sensitivity of the filter to the original shape. A different type of filter, termed a composite filter, was introduced to overcome these limitations. The reader is invited to refer to the following document for additional information regarding this different type of composite filter: H. J. Caufield and W. T. Maloney, Improved discrimination in optical character recognition, Appl. Opt., 8, 2354, 1969. The contents of this document are incorporated herein by reference.

In accordance with specific implementations, filters can be designed by:

- Appropriately choosing one specific instance (because it represents characteristics which are, on average, common to all symbols of a given class) of a symbol and calculating from that image the filter against which all instances of that class of symbols will be compared; or
- Averaging many instances of a given to create a generic or 'template' image from which the filter is calculated. The computed filter is then called a composite filter since it incorporates the properties of many images (note that it is irrelevant whether the images are averaged before or after the Fourier transform operator is applied, provided that in the latter case, the additions are performed taking the Fourier domain phase into account).

The latter procedure forms the basis for the generation of composite filters. Thus composite filters are composed of the response of individual POF filters to the same symbol. Mathematically, this can be expressed by:

$$h_{comp}(x,y) = a_a h_a(x,y) + a_b h_b(x,y) + a_x h_x(x,y) \quad (5)$$

A filter generated in this fashion is likely to be more robust to minor signature variations as the irrelevant high frequency features will be averaged out. In short, the net effect is an equalization of the response of the filter to the different instances of a given symbol.

Composite filters can also be used to reduce the response of the filter to the other classes of symbols. In equation (5) above, if the coefficient b, for example, is set to a negative value, then the filter response to a symbol of class b will be significantly reduced. In other words, the correlation peak will be high if $h_a(x,y)$ is at the input image, and low if $h_b(x,y)$ is present at the input. A typical implementation of composite filters is described in: Optical character recognition (OCR) in uncontrolled environments using optical correlators, Andre Morin, Alain Bergeron, Donald Prevost, and Ernst A. Radloff Proc. SPIE Int. Soc. Opt. Eng. 3715, 346 (1999). The contents of this document are incorporated herein by reference.

Typical Interaction

In accordance with a specific example of use of the system 100 depicted in FIG. 1, a manifest is generated for a given cargo container 104, the manifest describing the contents of the cargo container 104 at a departure location and therefore the contents expected to be present in the cargo container at an destination location. The cargo container 104 and its associated manifest are then shipped to another location geographically distinct from the departure location. For the purpose of simplicity and of this example, let us say that the other location is the destination location although it will be understood that the other location may also be an intermediate location between the departure location and the destination location. In a non-limiting implementation, the departure location may be a port in Hong Kong and the destination location may be a port in L.A. (USA). The manner in which the manifest is sent is not critical and it may be sent in any suitable format including electronic format and paper format.

The manifest is received at a processing station associated with the destination location and provided at input 120. An image of the cargo container 104 is obtained at the destination location by an image gathering device 102, the image conveying information related to contents of the cargo container 104. The image associated with the cargo container 104 is then processed by the cargo verification apparatus 106 in the manner described above in combination with the manifest received at input 120 and database of target images 110 to verify the contents of the cargo container 104.

Specific Physical Implementation

Figure 12:
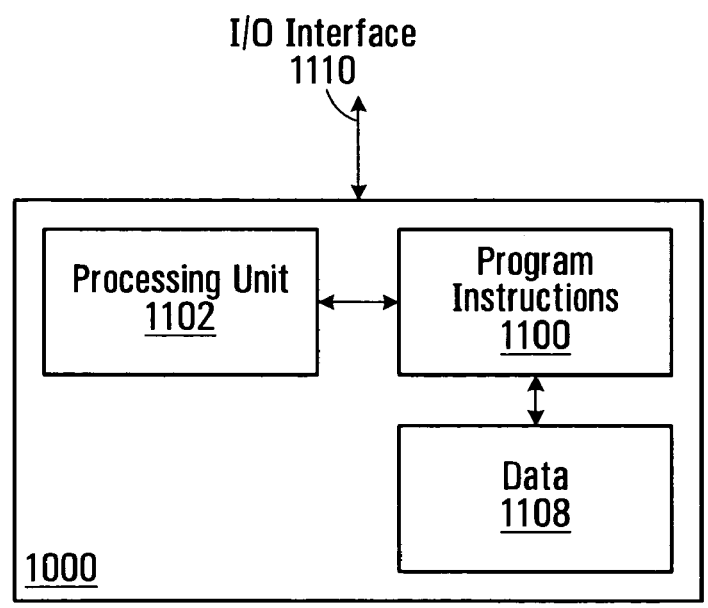
FIG. 12 is a block diagram of an apparatus suitable for implementing at least a portion of the modules depicted in connection with the apparatus for processing images shown in FIG. 3 in accordance with a specific example of implementation of the present invention.

Certain portions of the cargo verification apparatus 106 can be implemented on a general purpose digital computer 1100, of the type depicted in FIG. 12, including a processing unit 1102 and a memory 1104 connected by a communication bus. The memory includes data 1108 and program instructions 1106. The processing unit 1102 is adapted to process the data 1108 and the program instructions 1106 in order to implement the functional blocks described in the specification and depicted in the drawings. The digital computer 1100 may also comprise an I/O interface 1110 for receiving or sending data elements to external devices.

Alternatively, the above-described cargo verification apparatus 106 can be implemented on a dedicated hardware platform where electrical/optical components implement the functional blocks described in the specification and depicted in the drawings. Specific implementations may be realized using ICs, ASICs, DSPs, FPGA, an optical correlator, digital correlator or other suitable hardware platform.

Figure 13:
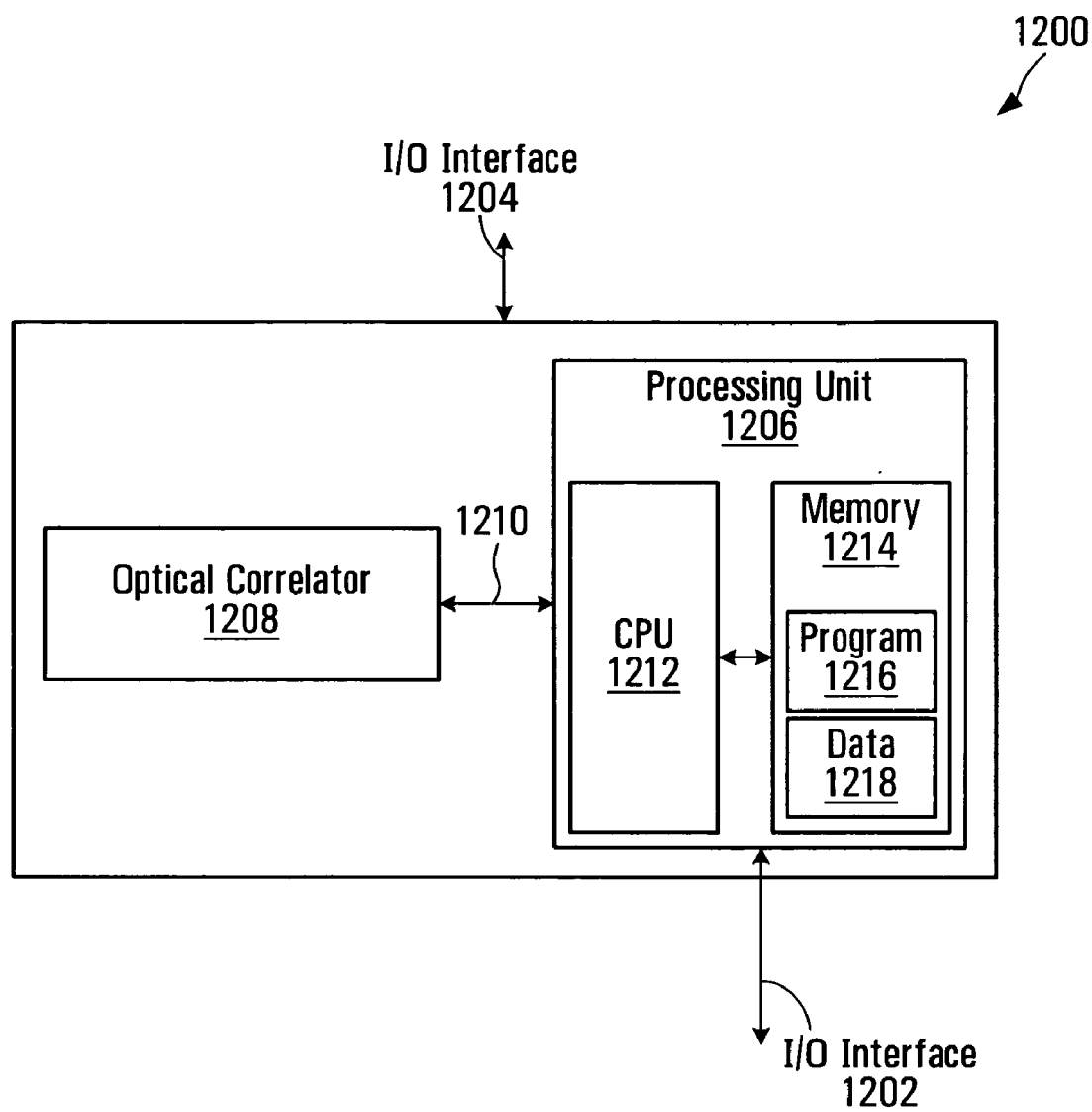
FIG. 13 is a block diagram of an alternative implementation of an apparatus suitable for implementing at least a portion of the modules depicted in connection with the apparatus for processing images shown in FIG. 3 in accordance with a specific example of implementation of the present invention.

Another alternative implementation of the cargo verification apparatus 106 can be implemented as a combination of dedicated hardware and software such as apparatus 1200 of the type depicted in FIG. 13. As shown, such an implementation comprises an optical correlator 1208 or other dedicated image processing hardware and a general purpose computing unit 1206 including a CPU 1212 and a memory 1214 connected by a communication bus. The memory includes data 1218 and program instructions 1216. The CPU 1212 is adapted to process the data 1218 and the program instructions 1216 in order to implement the functional blocks described in the specification and depicted in the drawings. The CPU 1212 is also adapted to exchange data with the optical correlator 1208 over communication link 1210 to make use of the optical correlator's image processing capabilities. The apparatus 1202 may also comprise I/O interfaces 1202 1204 for receiving or sending data elements to external devices.

In a variant, a single optical correlator 1208 can be shared by multiple general purpose computing units 1206. In such a variant, conventional parallel processing techniques can be used for sharing a common hardware resource.

In a specific example of implementation, the optical correlator suitable for use in the system described includes two video inputs. The video inputs are suitable for receiving a signal derived from an image generation device and a signal derived from a database of target images. In a specific implementation, the video inputs are suitable for receiving a signal in an NTSC compatible format or a VGA compatible format. It will be appreciated that either one of the video inputs may be adapted for receiving signals of lower or higher resolution than the VGA compatible format signal. Similarly, it will also be appreciated that the video input suitable for receiving a signal in an NTSC compatible format may be adapted for receiving signals in suitable formats such as, but not limited to, PAL and SECAM. In a non-limiting implementation, the optical correlator is adapted to process an image received at the video input having an area of 640×480 pixels. However, it will be readily apparent that, by providing suitable interfaces, larger or smaller images can be handled since the optical correlator's processing capability is independent of the size of the image, as opposed to digital systems that require more processing time and power as images get larger.

Figure 14:
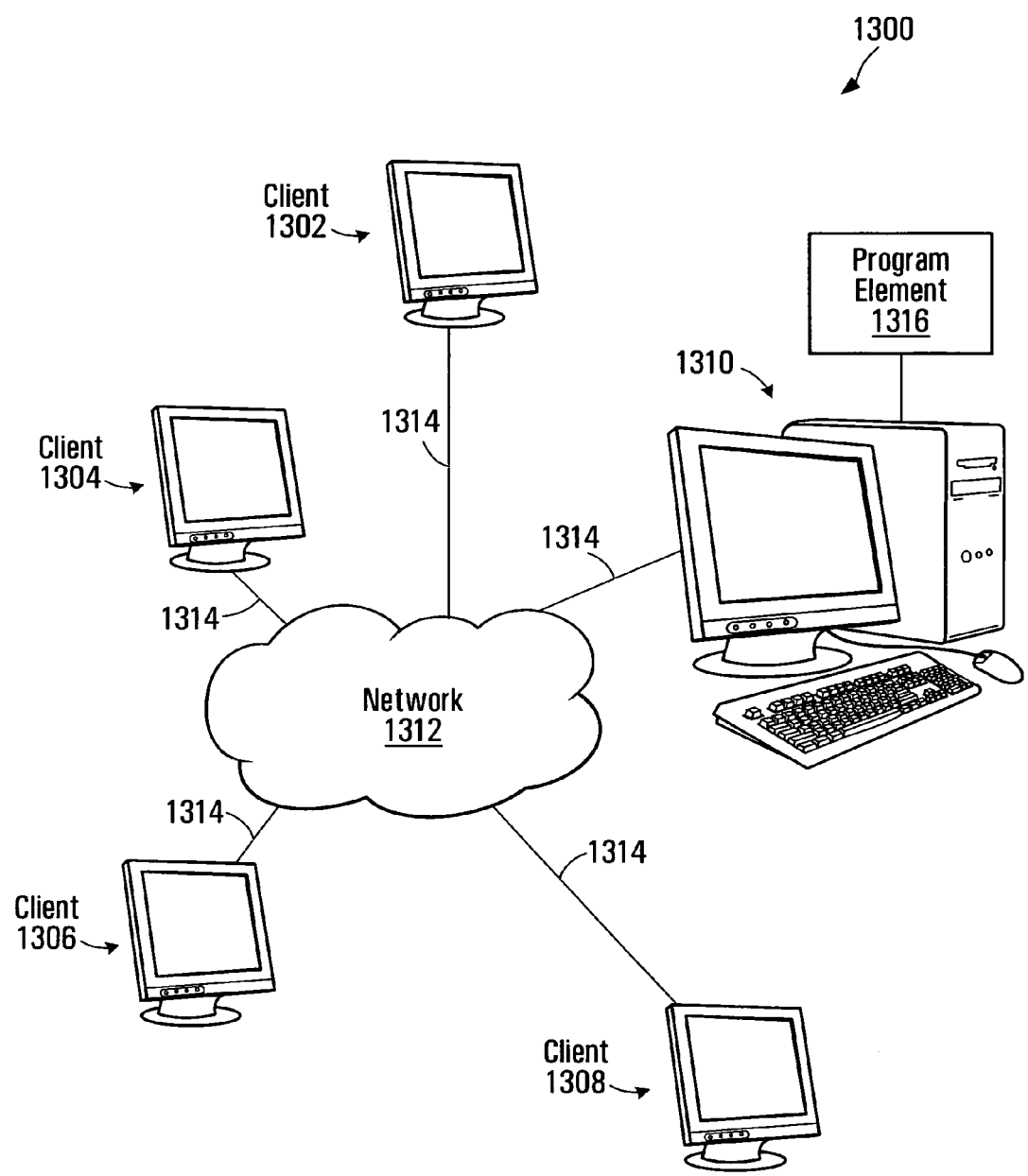
FIG. 14 shows a functional block diagram of a client-server system suitable for use in screening a cargo container in accordance with an alternative specific example of implementation of the present invention.

It will be appreciated that the system for screening cargo containers 100 (depicted in FIG. 1) may also be of a distributed nature where the image signals associated with the cargo containers are obtained at one location or more locations and transmitted over a network to a server unit implementing the method described above. The server unit may then transmit a signal for causing an output unit to convey mismatch information to the user. The output unit may be located in the same location where the image signal associated with the cargo container was obtained or in the same location as the server unit or in yet another location. In a non-limiting implementation, the output unit is part of a centralized cargo screening facility. FIG. 14 illustrates a network-based client-server system 1300 for system for screening cargo containers. The client-server system 1300 includes a plurality of client systems 1302, 1304, 1306 and 1308 connected to a server system 1310 through network 1312. The communication links 1314 between the client systems 1302, 1304, 1306 and 1308 and the server system 1310 can be metallic conductors, optical fibres or wireless, without departing from the spirit of the invention. The network 1312 may be any suitable network including but not limited to a global public network such as the Internet, a private network and a wireless network. The server 1310 may be adapted to process and issue signals concurrently using suitable methods known in the computer related arts.

The server system 1310 includes a program element 1316 for execution by a CPU. Program element 1316 includes functionality to implement the methods described above and includes the necessary networking functionality to allow the server system 1310 to communicate with the client systems 1302, 1304, 1306 and 1308 over network 1312. Optionally, server system 1310 also includes an optical correlator unit.

Although the present invention has been described in considerable detail with reference to certain preferred embodiments thereof, variations and refinements are possible without departing from the spirit of the invention. Therefore, the scope of the invention should be limited only by the appended claims and their equivalents.

The invention claimed is:

1. A method for screening a cargo container, said method being implemented by a computing apparatus having a processor, said method comprising:
   a) receiving at said computing apparatus image data associated with the cargo container and conveying information related to contents of the cargo container, said image data being derived by subjecting the cargo container to penetrating radiation;
   b) receiving at said computing apparatus a list of objects conveying objects expected to be present in the cargo container;
   c) using the processor of said computing apparatus;
      i. obtaining a group of target images based at least in part on the list of objects, the target images in said group corresponding to respective objects in the list of objects; and
      ii. processing the image data associated with the cargo container in combination with the group of target images to derive mismatch information data, said mismatch information data conveying at least one distinction between the list of objects and the information related to the contents of the cargo container conveyed by the image data;
   d) releasing at an output of said computing apparatus the mismatch information data.

2. A method as defined in claim 1, wherein said list of objects is a first list of objects, said method comprising:
   a) using the processor of said computing apparatus, processing the image data associated with the cargo container in combination with the group of target images to detect a presence of at least one object in the cargo container;
   b) using the processor of said computing apparatus, generating a second list of objects, the second list of objects conveying objects whose presence in the container was detected on the basis of the processing in a);
   c) using the processor of said computing apparatus, comparing the second list of objects with the first list of objects to derive the mismatch information data.

3. A method as defined in claim 2, wherein said mismatch information data conveys at least one object present in the first list of objects but absent from the second list of objects.

4. A method as defined in claim 2, wherein said first list of objects is derived from a manifest associated with the container.

5. A method as defined in claim 4, wherein obtaining the group of target images includes processing a database of target images on the basis of the first list of objects, the group of target images being a subset of the database of target images.

6. A method as defined in claim 1, wherein said image data conveys an x-ray image.

7. A method as defined in claim 1, wherein said method comprises using the processor of said computing apparatus to cause a display unit to convey the mismatch information data to a human operator.

8. A method as defined in claim 1, wherein said computing apparatus has access to a computer readable storage medium, said method comprises:
   a) using the processor of said computing apparatus, generating log information data elements conveying the mismatch information data;
   b) storing said log information data elements on the computer readable storage medium.

9. A method as defined in claim 8, wherein said log information data elements include a time stamp data element.

10. A method as defined in claim 2, wherein processing the image data associated with the container in combination with the group of target images to detect a presence of at least one object in the container comprises effecting a correlation operation between data derived from the image data and at least one target image in the group of target images.

11. A method as defined by claim 10, wherein said correlation operation is effected at least in part by an optical correlator.

12. A method as defined by claim 10, wherein said correlation operation is effected at least in part by a digital correlator.

13. A method as defined in claim 1, wherein the image data associated with the cargo container conveys a two-dimensional image.

14. A method as defined in claim 1, wherein the image data associated with the cargo container conveys a three-dimensional image.

15. A method as defined in claim 4, wherein said cargo container is associated to a cargo identifier data element, said method comprising using the processor of said computing apparatus for processing the cargo identifier data element in combination with a cargo container database to identify a manifest associated with the cargo container.

16. A method as define in claim 1, wherein the image data associated with the cargo container is derived by subjecting the cargo container to penetrating radiation using at least two sources of penetrating radiation, the at least two sources being positioned in different orientations.

17. An apparatus for screening a cargo container, said apparatus comprising:
- a) a first input for receiving image data associated with the cargo container and conveying information related to the contents of the cargo container, said image data being derived by subjecting the cargo container to penetrating radiation;
- b) a second input for receiving a first list of objects conveying objects expected to be present in the cargo container;
- c) a processing unit in communication with said first and second input, said processing unit being programmed for:
  - i. obtaining a group of target images based at least in part on the list of objects, the target images in said group corresponding to respective objects in the list of objects; and
  - ii. processing the image data associated with the cargo container in combination with the group of target images to derive mismatch information data, said mismatch information data conveying at least one distinction between the list of objects and the information related to the contents of the cargo container conveyed by the image data;
- d) an output for releasing the mismatch information data.

18. An apparatus as defined in claim 17, wherein said list of objects is a first list of objects, said processing unit being operative for:
- a) processing the image data associated with the cargo container in combination with the group of target images to detect a presence of at least one object in the cargo container;
- b) generating a second list of objects, the second list of objects conveying objects whose presence in the container was detected on the basis of the processing in a);
- c) comparing the second list of objects with the first list of objects to derive the mismatch information data.

19. An apparatus as defined in claim 18, wherein said mismatch information data conveys at least one object present in the first list of objects but absent from the second list of objects.

20. An apparatus as defined in claim 18, wherein said first list of objects is derived from a manifest associated with the container.

21. An apparatus as defined in claim 20, wherein obtaining the group of target images includes processing a database of target images on the basis of the first list of objects, the group of target images being a subset of the database of target images.

22. An apparatus as defined in claim 17, wherein said image data conveys an x-ray image.

23. An apparatus as defined in claim 18, wherein said output is adapted for releasing a signal for causing a display unit to convey the mismatch information data.

24. An apparatus as defined in claim 18, wherein said processing unit is programmed for:
- a) generating log information data elements conveying the mismatch information data;
- b) storing said log information data elements on a computer readable storage medium.

25. An apparatus as defined in claim 24, wherein said log information data elements include a time stamp data element.

26. An apparatus as defined in claim 18, wherein processing the image data associated with the container in combination with a group of target images to detect a presence of at least one object in the container comprises effecting a correlation operation between data derived from the image data and at least one target image in the group of target images.

27. An apparatus as defined by claim 26, wherein said correlation operation is effected at least in part by an optical correlator.

28. An apparatus as defined by claim 26, wherein said correlation operation is effected at least in part by a digital correlator.

29. An apparatus as defined in claim 18, wherein the image data associated with the cargo container conveys a two-dimensional image.

30. An apparatus as defined in claim 18, wherein the image data associated with the cargo container conveys a three-dimensional image.

31. An apparatus as defined in claim 20, wherein said cargo container is associated to a cargo identifier data element, said processing unit being operative for processing the cargo identifier data element in combination with a cargo container database to identify a manifest associated with the cargo container.

32. An apparatus as defined in claim 18, wherein said group of target images includes data elements indicative of Fourier transforms of target images.

33. An apparatus as defined in claim 18, wherein said processing unit includes an optical correlator, said optical correlator being operative for:
- a) processing the image data associated with the cargo container to derive a first
Fourier transform data element, said first Fourier transform data element being indicative of a Fourier transform of the image data associated with the cargo container;
- b) computing a correlation operation between the first Fourier transform data element and at least one Fourier transform of target images to detect a presence of at least one target object in the cargo container.

34. A system for screening cargo containers, said system comprising:
- a) an image generation device suitable for using penetrating radiation to generate image data associated with a cargo container and conveying information related to the contents of the cargo container;
- b) an apparatus in communication with said image generation device, said apparatus comprising:
  - i. a first input for receiving the image data associated with the cargo container;
  - ii. a second input for receiving a list of objects conveying objects expected to be present in the cargo container;
  - iii. a processing unit in communication with said first and second input, said processing unit being programmed for:
    - (a) obtaining a group of target images based at least in part on the list of objects, the target images in said group corresponding to respective objects in the list of objects; and
    - (b) processing the image data associated with the cargo container in combination with the group of target images to derive mismatch information data, said mismatch information data conveying at least one distinction between the list of objects and the information related to the contents of the cargo container conveyed by the image data;

iv. an output for releasing the mismatch information data;

c) an output module for conveying to a user of the system information derived at least in part on the basis of said mismatch information data.

35. A system as defined in claim 34, wherein said list of objects is a first list of objects, said processing unit being operative for:

a) processing the image data associated with the cargo container in combination with the group of target images to detect a presence of at least one object in the cargo container;

b) generating a second list of objects, the second list of objects conveying objects whose presence in the container was detected on the basis of the processing in a);

c) comparing the second list of objects with the first list of objects to derive the mismatch information data.

36. A system as defined in claim 35, wherein said mismatch information data conveys at least one object present in the first list of objects but absent from the second list of objects.

37. A system as defined in claim 35, wherein said first list of objects is derived from a manifest associated with the container.

38. A system as defined in claim 37, wherein obtaining the group of target images includes processing a database of target images on the basis of the first list of objects, the group of target images being a subset of the database of target images.

39. A system as defined in claim 35, wherein said output module includes a display screen for conveying to a user of the system information derived at least in part on the basis of said mismatch information in visual format.

40. A system as defined in claim 35, wherein said output module includes an audio output for conveying to a user of the system information derived at least in part on the basis of said mismatch information in audio format.

41. A system as defined in claim 35, wherein said processing unit is programmed for:

a) generating log information data elements conveying the mismatch information;

b) storing said log information data elements on a computer readable storage medium.

42. A system as defined in claim 35, wherein processing the image data associated with the container in combination with a group of target images to detect a presence of at least one object in the container comprises effecting a correlation operation between data derived from the image data and at least one target image in the group of target images.

43. A system as defined by claim 42, wherein said correlation operation is effected at least in part by an optical correlator.

44. A system as defined by claim 42, wherein said correlation operation is effected at least in part by a digital correlator.

45. A system as defined in claim 34, wherein the penetrating radiation is selected from the set consisting of x-ray, gamma-ray, computed tomography (CT scans) and millimeter wave.

46. A system as defined in claim 37, wherein said cargo container is associated to a cargo identifier data element, said processing unit being operative for processing the cargo identifier data element in combination with a cargo container database to identify a manifest associated with the cargo container.

47. A system as defined in claim 35, wherein said group of target images includes data elements indicative of Fourier transforms of target images.

48. A system as defined in claim 47, wherein said processing unit includes an optical correlator, said optical correlator being operative for:

a) processing the image data associated with the cargo container to derive a first Fourier transform data element, said first Fourier transform data element being indicative of a Fourier transform of the image data associated with the cargo container;

b) computing a correlation operation between the first Fourier transform data element and at least one Fourier transform of target images to detect a presence of at least one target object in the cargo container.

49. A computer readable medium including a program element suitable for execution by a computing apparatus for screening a cargo container, said computing apparatus comprising a memory unit and a processor operatively connected to said memory unit, said program element when executing on said processor being operative for:

a) receiving image data associated with the cargo container and conveying information related to the contents of the cargo container, said image data being derived by subjecting the cargo container to penetrating radiation;

b) receiving a first list of objects conveying objects expected to be present in the cargo container;

c) obtaining a group of target images based at least in part on the list of objects, the target images in said group corresponding to respective objects in the list of objects;

d) processing the image data associated with the cargo container in combination with the group of target images to detect a presence of at least one object in the cargo container;

e) generating a second list of objects, the second list of objects conveying objects whose presence in the container was detected in d);

f) comparing the second list of objects with the first list of objects to derive mismatch information data, said mismatch information data conveying at least one distinction between the first list of objects and the second list of objects;

g) releasing the mismatch information data.

50. A computer readable medium as defined in claim 49, wherein said mismatch information data conveys at least one object present in the first list of objects but absent from the second list of objects.

51. A computer readable medium as defined in claim 49, wherein said first list of objects is derived from a manifest associated with the container.

52. A computer readable medium as defined in claim 51, wherein said program element when executing on said processor being operative for obtaining the group of target images by processing a database of target images on the basis of the first list of objects, the group of target images being a subset of the database of target images.

53. A computer readable medium as defined in claim 49, wherein said program element when executing on said processor being operative for causing a display unit to convey the mismatch information data.

54. A computer readable medium as defined in claim 49, wherein said program element when executing on said processor being operative for:

a) generating log information data elements conveying the mismatch information data;

b) storing said log information data elements on a memory unit.

55. A computer readable medium as defined in claim 54, wherein said log information data elements include a time stamp data element.

56. A computer readable medium as defined in claim 51, wherein said cargo container is associated to a cargo identifier data element, said program element when executing on said processor being operative for processing the cargo identifier data element in combination with a cargo container database to identify a manifest associated with the cargo container.

57. An apparatus for screening a cargo container, said apparatus comprising:
 a) means for receiving image data associated with the cargo container and conveying information related to the contents of the cargo container, said image data being derived by subjecting the cargo container to penetrating radiation;
 b) means for receiving a list of objects conveying objects expected to be present in the cargo container;
 c) means for obtaining a group of target images based at least in part on the list of objects, the target images in said group corresponding to respective objects in the list of objects;
 d) means for processing the image data associated with the cargo container in combination with the group of target images to derive mismatch information data, said mismatch information data conveying at least one distinction between the first list of objects and the information related to the contents of the cargo container conveyed by the image data;
 e) means for releasing the mismatch information data.

* * * * *

UNITED STATES PATENT AND TRADEMARK OFFICE
CERTIFICATE OF CORRECTION

PATENT NO.        : 7,734,102 B2
APPLICATION NO. : 11/268749
DATED             : June 8, 2010
INVENTOR(S)       : Eric Bergeron, Luc Perron and Alain Bergeron It is certified that error appears in the above-identified patent and that said Letters Patent is hereby corrected as shown below:

In the specification:

- The mathematical expression (5) at column 23, line 31 should read as follows:

"$hcomp(x,y) = \alpha_a ha(x,y) + \alpha_b hb(x,y) + \ldots + \alpha_x hx(x,y)$"

- Please amend the paragraph beginning at column 24, line 15 as follows:

"Certain portions of the cargo verification apparatus 106 can be implemented on a general purpose digital computer ~~1100~~ 1000, of the type depicted in FIG.12, including a processing unit 1102 and a memory ~~1104~~ connected by a communication bus. The memory includes data 1108 and program instructions ~~1106~~ 1100. The processing unit 1102 is adapted to process the data 1108 and the program instructions ~~1106~~ 1100 in order to implement the functional blocks described in the specification and depicted in the drawings. The digital computer ~~1100~~ 1000 may also comprise an I/O interface 1110 for receiving or sending data elements to external devices."

In the claims:

Column 27, line 4

- Claim 16 should read as follows:

"A method as defined" instead of "A method as define".

Signed and Sealed this

Twenty-sixth Day of October, 2010

David J. Kappos
*Director of the United States Patent and Trademark Office*